United States Patent
Volles et al.

(10) Patent No.: US 12,359,199 B2
(45) Date of Patent: Jul. 15, 2025

(54) REGULATION OF GENE EXPRESSION VIA APTAMER-MEDIATED CONTROL OF SELF-CLEAVING RIBOZYMES

(71) Applicant: MEIRAGTX UK II LIMITED, London (GB)

(72) Inventors: Michael J. Volles, Cambridge, MA (US); Olivier F. Danos, New York, NY (US); Alex R. Boyne, Jersey City, NJ (US); Veronique Zennou, Jersey City, NJ (US); Xuecui Guo, Oyster Bay, NY (US)

(73) Assignee: MeiraGTX UK II Limited, London (GB)

( * ) Notice: Subject to any disclaimer, the term of this patent is extended or adjusted under 35 U.S.C. 154(b) by 0 days.

(21) Appl. No.: 18/059,606

(22) Filed: Nov. 29, 2022

(65) Prior Publication Data
US 2023/0220382 A1 Jul. 13, 2023

Related U.S. Application Data

(62) Division of application No. 16/074,681, filed as application No. PCT/US2017/016303 on Feb. 2, 2017, now Pat. No. 11,512,310.

(60) Provisional application No. 62/290,187, filed on Feb. 2, 2016, provisional application No. 62/290,209, filed on Feb. 2, 2016.

(51) Int. Cl.
*C12N 15/11* (2006.01)
*C12N 15/113* (2010.01)
*C12N 15/115* (2010.01)
*C12N 15/86* (2006.01)

(52) U.S. Cl.
CPC .......... *C12N 15/111* (2013.01); *C12N 15/113* (2013.01); *C12N 15/115* (2013.01); *C12N 15/86* (2013.01); *C12N 2310/12* (2013.01); *C12N 2310/121* (2013.01); *C12N 2310/16* (2013.01); *C12N 2310/3519* (2013.01); *C12N 2830/50* (2013.01); *C12N 2830/52* (2013.01)

(58) Field of Classification Search
CPC ...................... C12N 15/115; C12N 2310/3519
See application file for complete search history.

(56) References Cited

U.S. PATENT DOCUMENTS

| | | |
|---|---|---|
| 2009/0270485 A1 | 10/2009 | Ko et al. |
| 2013/0004980 A1 | 1/2013 | Huang et al. |
| 2014/0142160 A1 | 5/2014 | Lee et al. |
| 2015/0056174 A1 | 2/2015 | Mulligan et al. |

OTHER PUBLICATIONS

Berens, C. et al., "Riboswitch Engineering—Making the all Important Second and Third Steps"; Current Opinion in Biotechnology (2015); vol. 31; pp. 10-15.
Eiler, D. et al., "Structural Basis for the Fast Self-Cleaving Reaction Catalyzed by the Twister Ribozyme"; PNAS (2014); vol. 111:36; pp. 13028-13033.
Felletti, M. et al., "Twister Ribozymes: From Synthetic Biology to in vivo Function Investigations"; Abstract No. MON-440, FEBS (2014); vol. 281:Suppl 1, pp. 400.
Felletti, M. et la., "Screening of Genetic Switches Based on the Twister Ribozyme Motif"; Methods in Molecular Biology (Clifton, NJ, USA); Jan. 1, 2016; Ch. 19; pp. 225-239.
Felletti, M. et al., "Screening of Genetic Switches based on Twister Ribozyme Motif" (retrived from the internet on Jun. 26, 2017) URL http://europepmc.org/abstract/med/26552830, Jan. 1, 2016; 2 pgs.
Jimenez, R. M. et al., "Chemistry and Biology of Self-Cleaving Ribozymes"; Trends Biochem. Sci. (2015); vol. 40:11; pp. 648-661.
Kobori, S. et al., "High-Throughput Assay and Engineering of Self-Cleaving Ribozymes by Sequencing"; NAR (2015); vol. 43:13, e85 (8 pgs.).
Link, K. H. et al., "Engineering Ligand-Responsive Gene-Control Elements: Lessons Learned from Natural Riboswitches"; Gene Therapy (2009); vol. 16:10; pp. 1189-1201.
Ogawa, A. et al., "An Artificial Aptazyme-Based Riboswitch and its Cascading System in *E. coli*"; ChemBioChem (2008); vol. 9:2: pp. 206-209.
Roth, A. et la., "A Widespread Self-Cleaving Ribozyme Class is Revealed by Bioninformatics"; Nat. Chem. Biol. (2014); vol. 10:1; pp. 56-60; (17 pgs).
Roth, A. et la., Supplementalry Information: "A Widespread Self-Cleaving Ribozyme Class is Revealed by Bioninformatics"; Nat. Chem. Biol. (2014); (21 pgs).

*Primary Examiner* — Ekaterina Poliakova-Georgantas
(74) *Attorney, Agent, or Firm* — Fox Rothschild LLP

(57) ABSTRACT

The invention provides polynucleotide constructs for the regulation of gene expression by aptamer-based modulation of self-cleaving ribozymes and methods of using the constructs to regulate gene expression in response to the presence or absence of a ligand that binds the aptamer. The invention further provides methods for making and using riboswitches that decrease target gene expression in response to an aptamer ligand as well as riboswitches that increase target gene expression in response to an aptamer ligand.

25 Claims, 13 Drawing Sheets

Specification includes a Sequence Listing.

ATG_waspGua16

10aa_waspGua16

REGULATION OF GENE EXPRESSION VIA APTAMER-MEDIATED CONTROL OF SELF-CLEAVING RIBOZYMES

FIELD OF THE INVENTION

The invention provides polynucleotide constructs for the regulation of gene expression by aptamer-based modulation of self-cleaving ribozymes and methods of using the constructs to regulate gene expression in response to the presence or absence of a ligand that binds the aptamer.

REFERENCE TO A SEQUENCE LISTING

This application includes a Sequence Listing submitted electronically as an xml file named SeqList2-162027-46302, created on Mar. 25, 2024, with a size of 83,436 bytes. The Sequence Listing is incorporated herein by reference.

BACKGROUND OF THE INVENTION

Small endonucleolytic ribozymes comprise RNA motifs of about 50-150 nucleotides ("nt") in length that have intrinsic RNA cleavage activity. There are several classes of small endonucleolytic ribozymes including hammerhead, and hairpin. Recently, new classes of self-cleaving ribozymes have been identified including twister, twister sister, pistol and hatchet.

The present invention utilizes ribozymes linked to aptamers to create polynucleotide cassettes for the regulation of target gene expression in response to the presence or absence of a ligand that binds the aptamer.

SUMMARY OF THE INVENTION

In one aspect, the present invention provides a polynucleotide cassette for the regulation of the expression of a target gene comprising a riboswitch that comprises a twister ribozyme linked by a stem to an aptamer, wherein the stem linking the twister ribozyme to the aptamer attaches to the ribozyme at the location of the P3 stem of the twister ribozyme and wherein the target gene is linked to the P1 stem of the twister ribozyme. In this context, the riboswitch is an "off riboswitch" because aptamer/ligand binding increases the ribonuclease function of the twister ribozyme leading to cleavage of the target gene RNA that contains the polynucleotide cassette and thereby reduces target gene expression. In one embodiment, the aptamer binds a small molecule ligand.

In one embodiment, the twister ribozyme is from *Nasonia vitripennis*. In one embodiment, the twister ribozyme comprises SEQ ID NO.:38. In one embodiment, the twister ribozyme is from an environmental sample. In one embodiment, the twister ribozyme comprises SEQ ID NO.:39.

In one embodiment, the P1 stem comprises sequence that lengthens the P1 stem of the twister ribozyme by 1 to 3 base pairs. In one embodiment, the P1 stem of the twister ribozyme is 3 to 9 base pairs. In one embodiment, the P1 stem of the twister ribozyme is 4 to 7 base pairs. In one embodiment, the P1 stem of the twister ribozyme is 6 base pairs. In one embodiment, the P1 stem of the twister ribozyme is 7 base pairs. In one embodiment, the P1 stem of the twister ribozyme is 8 base pairs.

In one embodiment, the stem linking the ribozyme to the aptamer comprises sequence from the ribozyme P3 stem and/or sequence from the aptamer P1 stem. In one, embodiment, the stem linking the ribozyme to the aptamer does not comprise sequence from the ribozyme P3 stem and/or does not comprise sequence from the aptamer P1 stem. In one embodiment, the stem linking the ribozyme to the aptamer is about 3 to about 7 base pairs long. In one embodiment, the stem linking the ribozyme to the aptamer is 3 to 7 base pairs long. In one embodiment, the stem linking the ribozyme to the aptamer is 4 base pairs long. In one embodiment, the stem linking the ribozyme to the aptamer is 3 base pairs long.

In another aspect, the present invention provides a method of modulating the expression of a target gene comprising:
(a) inserting a polynucleotide cassette comprising an off riboswitch described herein into a target gene,
(b) introducing the target gene comprising the polynucleotide cassette into a cell, and
(c) exposing the cell to a small molecule ligand that specifically binds the aptamer in an amount effective to decrease expression of the target gene.

In one embodiment, the polynucleotide cassette is inserted into the 5' untranslated region of the target gene, the 3' untranslated region of the target gene, and/or downstream of the translation start codon of the target gene.

In one embodiment, when the polynucleotide cassette is inserted downstream (i.e., 3') of the translation start codon of the target gene, the riboswitch is adjacent to the start codon. In other embodiments, the riboswitch is about 1 to about 100, about 1 to about 50, or about 1 to about 20 nucleotides from the start codon of the target gene. In one embodiment, the polynucleotide cassette comprises a 2A peptide sequence between the 3' end of the riboswitch and the target gene coding sequence. In one embodiment, the polynucleotide cassette comprises a linker sequence adjacent to the 2A peptide sequence.

In one embodiment, two or more of the polynucleotide cassettes are inserted into the target gene. In one embodiment, the two or more polynucleotide cassettes comprise different aptamers that specifically bind to different small molecule ligands. In one embodiment, the two or more polynucleotide cassettes comprise the same aptamer.

In one embodiment, the target gene comprising the polynucleotide cassette is incorporated in a vector for the expression of the target gene. In one embodiment, the vector is a viral vector. In one embodiment, the viral vector is selected from the group consisting of adenoviral vector, adeno-associated virus vector, and lentiviral vector.

In another aspect, the present invention provides a polynucleotide cassette for the regulation of the expression of a target gene comprising a riboswitch that comprises a twister ribozyme linked to an aptamer, wherein the aptamer is linked to the 3' or 5' end of the twister ribozyme P1 stem, wherein when the aptamer is linked to the 3' end of the twister ribozyme P1 stem, a portion of the 3' arm of the twister ribozyme P1 stem is alternatively the 5' arm of the aptamer P1 stem, and wherein when the aptamer is linked to the 5' end of the twister ribozyme P1 stem, a portion of the 5' arm of the twister ribozyme P1 stem is alternatively the 3' arm of the aptamer P1 stem (see, e.g., FIGS. 6a-6b). In this context, the riboswitch is an "on riboswitch" because aptamer/ligand binding inhibits the ribonuclease function of the twister ribozyme decreasing cleavage of the target gene RNA that contains the polynucleotide cassette and thereby increasing target gene expression. In one embodiment, the aptamer binds a small molecule ligand.

In one embodiment, the twister ribozyme is from *Nasonia vitripennis*. In one embodiment, the twister ribozyme comprises SEQ ID NO.:38. In one embodiment, the twister ribozyme is from an environmental sample. In one embodiment, the twister ribozyme comprises SEQ ID NO.:39.

In one embodiment, the portion of the arm of the twister ribozyme P1 stem that is alternatively an arm of the aptamer P1 stem is 4 to 8 nucleotides, 5 to 7 nucleotides, 6 nucleotides, or 7 nucleotides. In one embodiment, the P1 stem of the twister ribozyme is 4 to 9 base pairs, 5 to 8 base pairs, 6 base pairs, or 7 base pairs. In one embodiment, the P1 stem of the aptamer is 6 to 11 base pairs, 7 to 10 base pairs, 8 base pairs, or 9 base pairs.

In another aspect, the present invention provides a method of modulating the expression of a target gene comprising:
(a) inserting the polynucleotide cassette comprising an on riboswitch described herein into a target gene,
(b) introducing the target gene comprising the polynucleotide cassette into a cell, and
(c) exposing the cell to a small molecule ligand that specifically binds the aptamer in an amount effective to increase expression of the target gene.

In one embodiment, the polynucleotide cassette is inserted into the 5' untranslated region of the target gene, the 3' untranslated region of the target gene, and/or downstream of the translation start codon.

In one embodiment, when the polynucleotide cassette is inserted downstream (i.e., 3') of the translation start codon of the target gene, the on riboswitch is adjacent to the start codon. In other embodiments, the riboswitch is about 1 to about 100, about 1 to about 50, or about 1 to about 20 nucleotides from the start codon of the target gene. In one embodiment, the polynucleotide cassette comprises a 2A peptide sequence between the 3' end of the riboswitch and the target gene coding sequence. In one embodiment, the polynucleotide cassette comprises a linker sequence adjacent to the 2A peptide sequence.

In one embodiment, two or more of the polynucleotide cassettes are inserted into the target gene. In one embodiment, the two or more polynucleotide cassettes comprise different aptamers that specifically bind to different small molecule ligands. In one embodiment, the two or more polynucleotide cassettes comprise the same aptamer.

In one embodiment, the target gene comprising the polynucleotide cassette is incorporated in a vector for the expression of the target gene. In one embodiment, the vector is a viral vector. In one embodiment, the viral vector is selected from the group consisting of adenoviral vector, adeno-associated virus vector, and lentiviral vector.

In another aspect, the present invention provides vector comprising a target gene that contains a polynucleotide cassette of the present invention. In one embodiment, the vector is a viral vector. In one embodiment, the viral vector is selected from the group consisting of adenoviral vector, adeno-associated virus vector, and lentiviral vector.

BRIEF DESCRIPTION OF THE FIGURES

FIG. 1a. Twister ribozyme sequence from N. vitripennis (wasp-twister; see SEQ ID NO: 38) or from environmental sample (es-twister; see SEQ ID NO: 39) was cloned into the 3' untranslated region ("UTR") in pEGFP-C1 vector. HEK 293 cells were transfected with the indicated constructs and fluorescence intensity of GFP measured. Wasp-twister caused approximately 97% or 36-fold reduction in GFP expression when compared to pEGFP-C1 control. The es-twister when cloned into the 3' UTR of GFP significantly reduced target gene expression in HEK 293 cells, but not to the same extent as the wasp twister.

FIG. 1b. Mutant twister sequence (see SEQ ID NO: 40) was generated by mutating the A6 to G, as indicated by the wasp-twister secondary structure embedded in the graph. HEK 293 cells were transfected with the indicated constructs and fluorescence intensity of GFP measured. The wasp-twister again reduced expression of GFP when cloned into the 3' UTR. The wasp-twister Mutant, however, did not cause a reduction in GFP expression.

FIG. 2a. The sequence of 3 base pair extension (3HP) of the wasp twister P1 stem (see SEQ ID NO: 5).

FIG. 2b. Deletion of SacII site from the initial construct GFP_wasp-twister and addition of 3 bp stem to twister P1 stem improved cleavage by twister ribozyme, leading to further reduction in the GFP expression.

FIG. 3a. The schematics of the linking aptamer sequence to twister ribozyme and the rationale for aptamer ligand responsive twister ribozyme. Aptamer sequence was shown in thicker line. In the absence of aptamer ligand, the ligand free aptamer disrupts twister ribozyme cleavage, leading to intact mRNA and subsequent gene expression. In the presence of aptamer ligand, ligand bound aptamer facilitates the P3 stem formation, thus restoring the twister ribozyme cleavage activity, leading to inhibition of gene expression.

FIG. 3b. The results of firefly luciferase assay. Twenty constructs were made by linking the P1 stem of guanine aptamer to the P3 stem of the twister ribozyme, as shown in FIG. 3a, lower panel. The additional 3HP was counted in as part of the twister P1 stem. The stem that connects the Loop 2 and aptamer was truncated sequentially, generating different length of stems as indicated in the round brackets. HEK 293 cells were transfected with the indicated constructs, treated with or without guanine. The fold reduction for construct Luci-waspGua16 is indicated in the graph.

FIG. 3c. Validation of luciferase constructs containing waspGua16 or a mutant waspGua16. Wild type waspGua16 reduced luciferase activity upon treatment with 500 μM guanine, while the mutant waspGua16 did not.

FIG. 3d. shown is the results of luciferase assay. HEK 293 cells were transfected with the indicated constructs, and treated with or without 500 μM guanine or 1 mM guanosine.

FIG. 3e. HEK 293 cells were transfected with the indicated constructs, and treated with 500 μM guanosine. DMSO was used as solvent control. Supernatant was collected 18 hours after guanosine treatment, the Epo was measured using ELISA kit. The results were expressed as mean±SD (n=2). Shown is the representative of two independent experiments.

FIG. 4a. Schematic of the linking theophylline aptamer to the loop 2 sequence in twister ribozyme. The sequences and the length of the stem connecting theophylline aptamer and twister loop 2 were shown, including Twister_theo_1 (SEQ ID NO: 28), Twister_theo_2 (SEQ ID NO: 29), Twister_theo_3 (SEQ ID NO: 30), and Twister_theo_4 (SEQ ID NO: 31). The aptamer and ligand was indicated as  .

FIG. 4b. Shown are the results of the luciferase assay. HEK 293 cells were transfected with the indicated constructs, treated with and without 2 mM theophylline 4 hours after transfection.

FIG. 5a. The schematics of constructs with twisterGua16 riboswitch and a linker and 2A peptide sequence (linker2A) inserted downstream of ATG and upstream of the remaining luciferase coding sequence (top panel), or twisterGua16 and linker2A sequence inserted downstream the coding sequence for the first 10 amino acids of GFP (lower panel).

FIG. 5b. Result of a luciferase assay are shown. HEK 293 cells were transfected with the indicated constructs. The transfected cells were treated with or without guanine 4 hours after transfection. Results is expressed as mean±SD (n=3).

FIG. 6a. Shows the schematics of the ON twister guanine riboswitch (where the aptamer is linked to the 3' end of twister P1). The configuration of the wasp twister and aptamer sequence is shown as an example, in which the 3' end of the P1 stem (including the 3 bp stem) was linked to the aptamer sequence. In this configuration, the stem sequence was shared between the twister P1 stem and the aptamer P1 stem. The shared stem sequence is indicated as in thicker line. Presumably, in the absence of the aptamer ligand (top panel), aptamer sequence linked to the twister P1 stem does not disrupt twister structure and its ribozyme cleavage activity, therefore resulting in cleavage of mRNA and subsequent inhibition of gene expression. In the presence of aptamer ligand (lower panel), aptamer forms P1 stem and makes the shared stem sequence (thicker line) unavailable for twister P1 stem formation, therefore disrupting twister structure and its ribozyme activity, resulting in intact mRNA and subsequent gene expression.

FIG. 6b. HEK 293 cells were transfected with the indicated luciferase constructs. The transfected cells were treated with or without 500 µM guanosine. DMSO was used as solvent control. Results are expressed as mean±SD (n=3). The induction folds were indicated in the graph for each construct.

DETAILED DESCRIPTION OF THE INVENTION

Figure 1A:
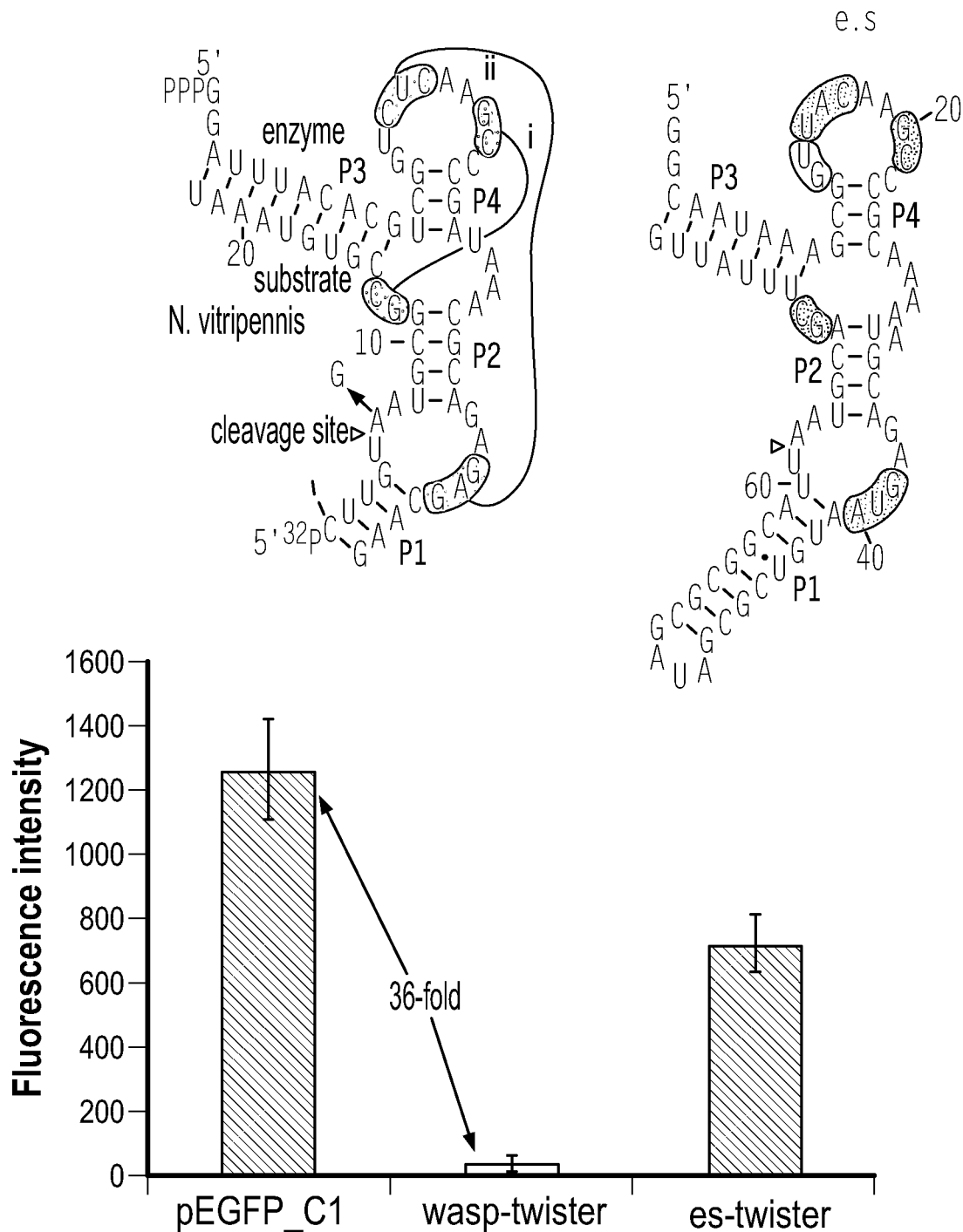
FIGS. 1a-1b. Twister ribozymes self-cleave and suppress gene expression in mammalian cells.

The invention provides polynucleotide constructs for the regulation of gene expression by aptamer-based modulation of small endonucleolytic ribozymes and methods of using the constructs to regulate gene expression in response to the presence or absence of a ligand that binds the aptamer. The polynucleotide construct contains at least one riboswitch that contains a ribozyme and an aptamer. The way the ribozyme is attached to the aptamer provides for riboswitches that activate ribozyme self-cleavage in the presence of aptamer ligand ("off" riboswitches) or riboswitches that inhibit ribozyme self-cleavage in the presence of aptamer ("on" riboswitches).

The gene regulation polynucleotide cassette refers to a recombinant DNA construct that, when incorporated into the DNA of a target gene, provides the ability to regulate expression of the target gene by aptamer/ligand mediated regulation of ribozyme self-cleavage. As used herein, a polynucleotide cassette or construct is a nucleic acid (e.g., DNA or RNA) comprising elements derived from different sources (e.g., different organisms, different genes from the same organism, and the like). The polynucleotide cassette comprises a riboswitch. The riboswitch in the context of the present invention contains a sensor region (e.g., an aptamer) and a ribozyme that together are responsible for sensing the presence of a ligand that binds the sensor region and altering the conformation of ribozyme binding site. In one embodiment, the target gene's expression is increased when the aptamer ligand is present and decreased when the ligand is absent. In another embodiment, the target gene's expression is decreased when the aptamer ligand is present and increased when the ligand is absent.

Ribozymes

The ribozyme used in the present invention can be any small endonucleolytic ribozyme that will self-cleave in the target cell type including, for example, hammerhead, hairpin, the hepatitis delta virus, the Varkud satellite, twister, twister sister, pistol and hatchet. See, e.g., Roth et al., Nat Chem Biol. 10(1):56-60; and Weinberg et al., Nat Chem Biol. 2015 August; 11(8):606-10, both incorporated herein by reference. U.S. 2015/0056174 provides modified hammerhead ribozymes with enhanced endonucleolytic activity (see, e.g., FIGS. 5A-F, incorporated herein by reference). Preferred ribozymes are hammerhead, hairpin, and twister. In one embodiment, the ribozyme is the twister ribozyme is from *Nasonia vitripenni* (SEQ. ID NO.:38). In one embodiment, the ribozyme is the twister ribozyme identified from an environmental sample (SEQ. ID NO.:39).

Riboswitch

The term "riboswitch" as used herein refers to a regulatory segment of a RNA polynucleotide. A riboswitch in the context of the present invention contains a sensor region (e.g., an aptamer) a self-cleaving ribonuclease that together are responsible for sensing the presence of a ligand (e.g., a small molecule) and modulating the conformation of a self-cleaving ribonuclease and thereby its activity. In one embodiment, the riboswitch is recombinant, utilizing polynucleotides from two or more sources. The term "synthetic" as used herein in the context of a riboswitch refers to a riboswitch that is not naturally occurring. In one embodiment, the sensor (e.g., aptamer) and ribonuclease regions are joined by a polynucleotide linker. In one embodiment, the polynucleotide linker forms a RNA stem (i.e., a region of the RNA polynucleotide that is double-stranded).

Off Riboswitches

Figure 3A:
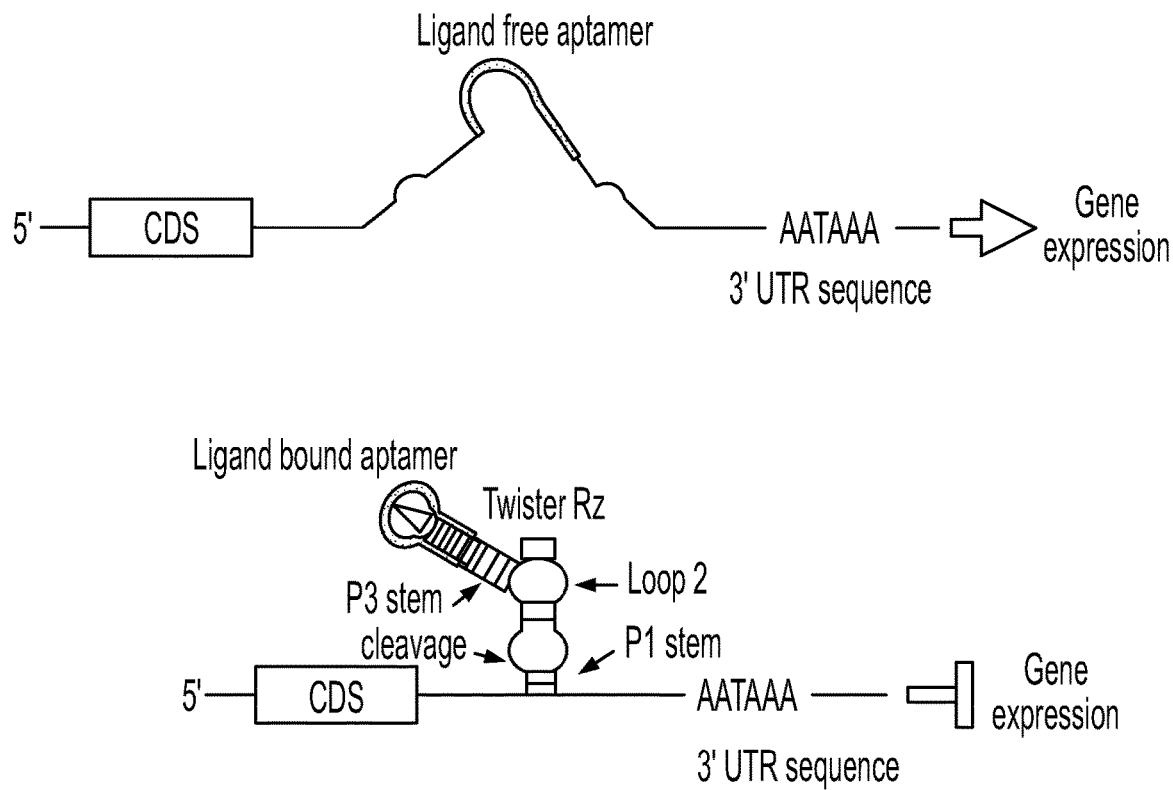
FIGS. 3a-3e. Generation of guanine-responsive twister ribozyme.

In one aspect, the present invention provides a polynucleotide cassette for the regulation of the expression of a target gene comprising a riboswitch that comprises a twister ribozyme linked by a stem to an aptamer, wherein the stem linking the twister ribozyme to the aptamer attaches to the ribozyme at the location of the P3 stem of the twister ribozyme, and wherein the target gene is linked to the P1 stem of the twister ribozyme (see, e.g., FIG. 3a). In this context, the riboswitch is an "off riboswitch" because aptamer/ligand binding increases the ribonuclease function of the twister ribozyme leading to cleavage of the target gene RNA that contains the polynucleotide cassette thereby reducing target gene expression.

In this configuration, where both arms of an aptamer stem are linked to both arms of the ribozyme P3 stem, this stem may contain additional sequence capable of forming a stem when the aptamer binds its ligand. This additional stem sequence may include sequence from the aptamer P1 stem and/or additional sequence added to facilitate stem formation when the aptamer is bound by its ligand. The P3 stem may comprise one, two, three or more changes from the wild-type P3 sequence for the ribozyme. In some embodiments, the stem linking the aptamer to the ribozyme does not contain sequence from either the P3 stem of twister or from the aptamer stem. In addition, the stem linking the ribozyme to the aptamer (including the P3 stem) may comprise one or more mismatches where a nucleotide is not complementary to its counterpart on the other stem arm.

The stem linking the aptamer to the ribozyme should be of a sufficient length (and GC content) to form a stem upon ligand binding the aptamer thereby promoting the ribozyme endonuclease activity, while also, when the ligand is not present in sufficient quantities, taking a conformation that inhibits ribozyme endonuclease activity. The length and sequence of the stem can be modified using known techniques in order to identify stems that allow acceptable background expression of the target gene when ligand is present and acceptable expression levels of the target gene when the ligand is not present. If the stem is, for example, too long it may provide an active ribozyme conformation in the presence or absence of ligand. If the stem is too short, it may not provide an active ribozyme even in the presence of ligand. In certain embodiments, the stem linking the ribozyme to the aptamer is about 3 to about 7 base pairs. In one embodiment, the stem linking the ribozyme to the aptamer is 3 to 7 base pairs. In one embodiment, the stem linking the ribozyme to the aptamer is 4 base pairs long. In one embodiment, the stem linking the ribozyme to the aptamer is 3 base pairs long.

It should be understood that the stem linking the aptamer and ribozyme is not always in a double-stranded stem configuration. As shown in FIG. 3a, when the aptamer is not bound to ligand, the structure of the stem is disrupted inhibiting ribozyme endonucleolytic activity. When the aptamer binds its ligand the stem is stabilized promoting ribozyme endonucleolytic activity.

In this off riboswitch configuration, the P1 stem of the ribozyme is linked to the nucleotide sequence of the target gene (see, e.g., FIG. 3a). This ribozyme P1 stem may comprise all or some of the P1 sequence of the naturally-occurring ribozyme. This P1 stem may contain additional stem sequence from another source. The P1 stem may comprise one, two, three or more changes from the wild-type P1 sequence for the ribozyme. In some embodiments, the P1 stem of the ribozyme does not contain any sequence from the wild-type P1 sequence for the ribozyme. The stem is still referred to as the P1 stem of the ribozyme by virtue of its location. The length and sequence of the P1 stem can be modified using known techniques in order to identify stems that allow, e.g., acceptable background expression of the target gene. In one embodiment, the P1 stem of the twister ribozyme is 3 to 9 base pairs. In one embodiment, the P1 stem of the twister ribozyme is 4 to 7 base pairs. In one embodiment, the P1 stem of the twister ribozyme is 7 base pairs. In one embodiment, the P1 stem of the twister ribozyme is 8 base pairs.

The polynucleotide cassette comprising the off riboswitch may be placed at one or more locations in the target gene, including, but not limited to the 5' and 3' UTR and downstream of the start codon.

On Riboswitches

Figure 6A:
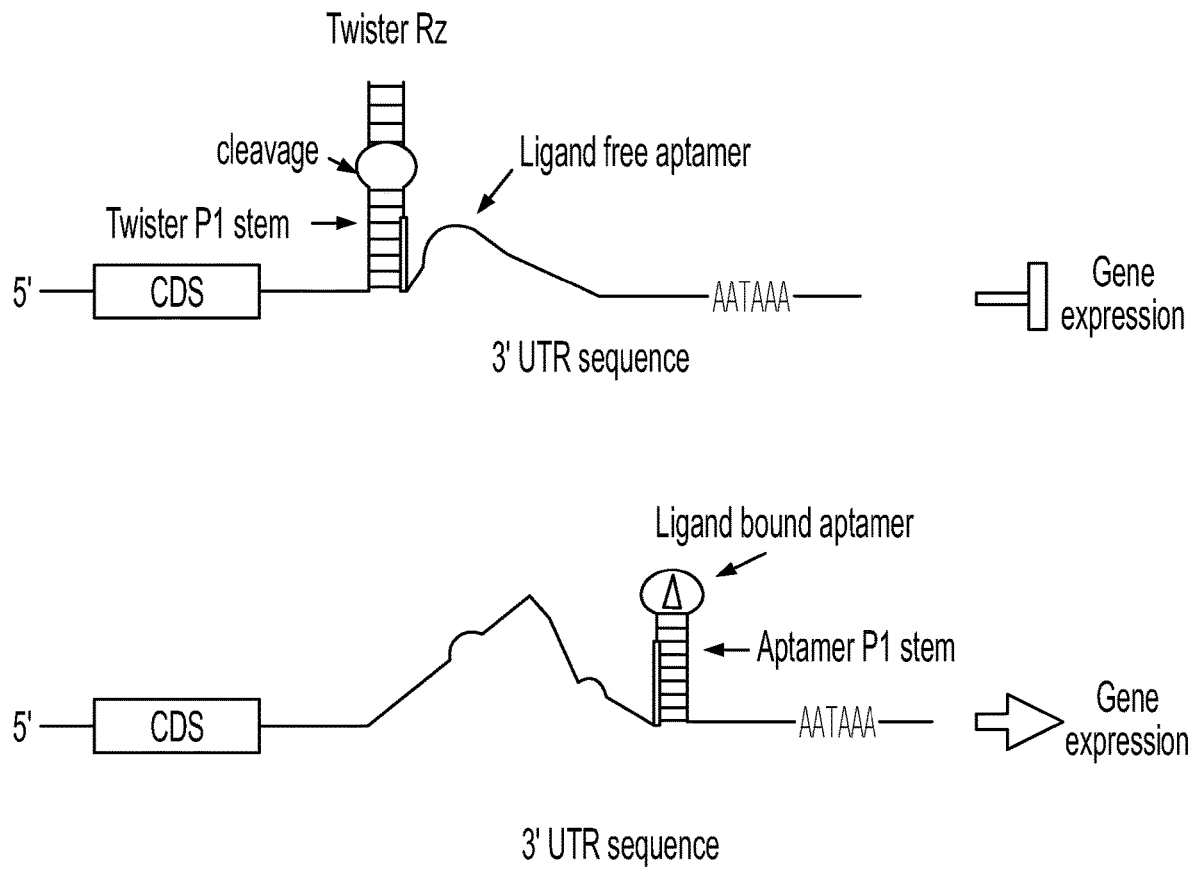
FIGS. 6a-6b. Generation of aptamer ligand responsive ON twister riboswitch.
Figure 6B:
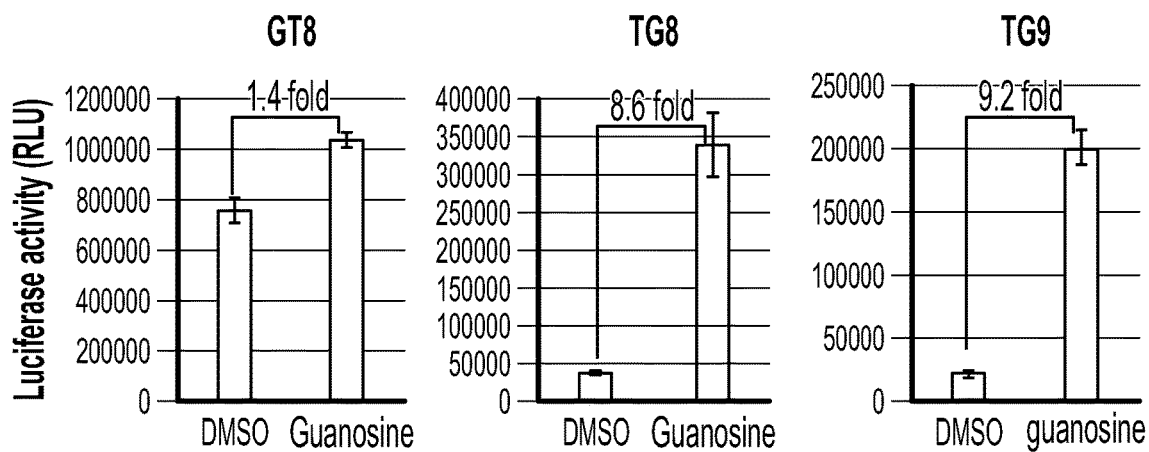

In another aspect, the present invention provides a polynucleotide cassette for the regulation of the expression of a target gene comprising a riboswitch that comprises a twister ribozyme linked to an aptamer, wherein the aptamer is linked to the 3' or 5' end of the twister ribozyme P1 stem, wherein when the aptamer is linked to the 3' end of the twister ribozyme P1 stem, a portion of the 3' arm of the twister ribozyme P1 stem is alternatively the part of the 5' arm of the aptamer P1 stem, and wherein when the aptamer is linked to the 5' end of the twister ribozyme P1 stem, a portion of the 5' arm of the twister ribozyme P1 stem is alternatively part of the 3' arm of the aptamer P1 stem (see, e.g., FIGS. 6a-6b). In this context, the riboswitch is an "on riboswitch" because aptamer/ligand binding inhibits the ribonuclease function of the twister ribozyme decreasing cleavage of the target gene RNA that contains the polynucleotide cassette and thereby increasing target gene expression in the presence of ligand.

As with the aptamer and ribozyme stems discussed with respect to off riboswitch, the ribozyme P1 stem and aptamer P1 stem may or may not comprise wild-type stem sequence. As such, the stem names are based on their location on the ribozyme or aptamer and does not imply that the stems comprise any particular sequence. The P1 ribozyme stem and the P1 aptamer stem may each independently comprise stem sequence in addition to the shared stem sequence. This additional stem sequence may include sequence from the respective ribozyme P1 or aptamer P1 stem and/or additional sequence added to facilitate stem formation. In addition, ribozyme P1 and/or aptamer P1 stem may comprise one or more mismatches where a nucleotide is not complementary to its counterpart on the other stem arm.

The ribozyme P1 and aptamer P1 stem should be of a sufficient length (and GC content) such that the aptamer forms the P1 stem in the presence of aptamer ligand and the ribozyme forms the P1 stem when ligand is not present. The length and sequence of the stems can be modified using known techniques in order to identify stems that allow acceptable background expression of the target gene when ligand is not present and acceptable expression levels of the target gene when the ligand is present. In one embodiment, P1 stem of the twister ribozyme is 4 to 9 base pairs, 5 to 8 base pairs, 6 base pairs, or 7 base pairs. In one embodiment, the P1 stem of the aptamer is 6 to 11 base pairs, 7 to 10 base pairs, 8 base pairs, or 9 base pairs.

In this on riboswitch configuration, the aptamer is adjacent to the ribozyme (either 5' or 3') and the aptamer and ribozyme both comprise an alternatively shared stem arm.

When the aptamer is bound to its ligand, it stabilizes the aptamer P1 stem, preventing its use as part of the ribozyme structure and inhibiting ribozyme endonuclease activity. When ligand is not present, the shared stem is free to form part of the ribozyme P1 stem, thereby allowing ribozyme endonuclease activity and cleavage of the target RNA leading to reduced target gene expression. In embodiments, the alternatively shared portion of the ribozyme and aptamer stems is 4 to 8 nucleotides, 5 to 7 nucleotides, 6 nucleotides, or 7 nucleotides.

The polynucleotide cassette comprising the on riboswitch may be placed at one or more locations in the target gene, including, but not limited to the 5' and 3' UTR and downstream of the start codon.

Aptamer/Ligand

In one embodiment, the sensor region comprises an aptamer. The term "aptamer" as used herein refers to an RNA polynucleotide that specifically binds to a ligand. The term "ligand" refers to a molecule that is specifically bound by an aptamer. In one embodiment, the ligand is a low molecular weight (less than about 1,000 Daltons) molecule including, for example, lipids, monosaccharides, second messengers, co-factors, metal ions, other natural products and metabolites, nucleic acids, as well as most therapeutic drugs. In one embodiment, the ligand is a polynucleotide with two or more nucleotide bases.

In one embodiment, the ligand is selected from the group consisting of 8-azaguanine, adenosine 5'-monophosphate monohydrate, amphotericin B, avermectin B1, azathioprine, chlormadinone acetate, mercaptopurine, moricizine hydrochloride, N6-methyladenosine, nadide, progesterone, promazine hydrochloride, pyrvinium pamoate, sulfaguanidine, testosterone propionate, thioguanosine, tyloxapol and vorinostat.

Aptamer ligands can also be cell endogenous components that increase significantly under specific physiological/pathological conditions, such as oncogenic transformation—these may include second messenger molecules such as GTP or GDP, calcium; fatty acids, or fatty acids that are incorrectly metabolized such as 13-HODE in breast cancer (Flaherty, J T et al., Plos One, Vol. 8, e63076, 2013, incorporated herein by reference); amino acids or amino acid metabolites; metabolites in the glycolysis pathway that usually have higher levels in cancer cells or in normal cells in metabolic diseases; and cancer-associated molecules such as Ras or mutant Ras protein, mutant EGFR in lung cancer, indoleamine-2,3-dioxygenase (IDO) in many types of cancers. Endogenous ligands include progesterone metabolites in breast cancer as disclosed by JP Wiebe (Endocrine-Related Cancer (2006) 13:717-738, incorporated herein by reference). Endogenous ligands also include metabolites with increased levels resulting from mutations in key metabolic enzymes in kidney cancer such as lactate, glutathione, kynurenine as disclosed by Minton, D R and Nanus, D M (Nature Reviews, Urology, Vol. 12, 2005, incorporated herein by reference).

Aptamers have binding regions that are capable of forming complexes with an intended target molecule (i.e., the ligand). The specificity of the binding can be defined in terms of the comparative dissociation constants (Kd) of the aptamer for its ligand as compared to the dissociation constant of the aptamer for unrelated molecules. Thus, the ligand is a molecule that binds to the aptamer with greater affinity than to unrelated material. Typically, the Kd for the aptamer with respect to its ligand will be at least about 10-fold less than the Kd for the aptamer with unrelated molecules. In other embodiments, the Kd will be at least about 20-fold less, at least about 50-fold less, at least about 100-fold less, and at least about 200-fold less. An aptamer will typically be between about 15 and about 200 nucleotides in length. More commonly, an aptamer will be between about 30 and about 100 nucleotides in length.

The aptamers that can be incorporated as part of the riboswitch can be a naturally occurring aptamer, or modifications thereof, or aptamers that are designed de novo and/or screened through systemic evolution of ligands by exponential enrichment (SELEX) or other screening methods. Examples of aptamers that bind small molecule ligands include, but are not limited to theophylline, dopamine, sulforhodamine B, cellobiose, kanamycin A, lividomycin, tobramycin, neomycin B, viomycin, chloramphenicol, streptomycin, cytokines, cell surface molecules, and metabolites. For a review of aptamers that recognize small molecules, see, e.g., Famulok, Science 9:324-9 (1999) and McKeague, M. & DeRosa, M. C. J. Nuc. Aci. 2012 (both of which are incorporated herein by reference). In another embodiment, the aptamer is a complementary polynucleotide.

Methods for Identifying Aptamer/Ligand

In one embodiment, the aptamer is designed to bind a particular small molecule ligand. Methods for designing and selecting aptamers that bind particular ligands are disclosed in 62/370,599, incorporated herein by reference. Other methods for screening aptamers include, for example, SELEX. Methods for designing aptamers that selectively bind a small molecule using SELEX are disclosed in, e.g., U.S. Pat. Nos. 5,475,096, 5,270,163, and Abdullah Ozer, et al. Nuc. Aci. 2014, which are incorporated herein by reference. Modifications of the SELEX process are described in U.S. Pat. Nos. 5,580,737 and 5,567,588, which are incorporated herein by reference.

Selection techniques for identifying aptamers generally involve preparing a large pool of DNA or RNA molecules of the desired length that contain a region that is randomized or mutagenized. For example, an oligonucleotide pool for aptamer selection might contain a region of 20-100 randomized nucleotides flanked by regions of defined sequence that are about 15-25 nucleotides long and useful for the binding of PCR primers. The oligonucleotide pool is amplified using standard PCR techniques, or other means that allow amplification of selected nucleic acid sequences. The DNA pool may be transcribed in vitro to produce a pool of RNA transcripts when an RNA aptamer is desired. The pool of RNA or DNA oligonucleotides is then subjected to a selection based on their ability to bind specifically to the desired ligand. Selection techniques include, for example, affinity chromatography, although any protocol which will allow selection of nucleic acids based on their ability to bind specifically to another molecule may be used. Selection techniques for identifying aptamers that bind small molecules and function within a cell may involve cell based screening methods. In the case of affinity chromatography, the oligonucleotides are contacted with the target ligand that has been immobilized on a substrate in a column or on magnetic beads. The oligonucleotide is preferably selected for ligand binding in the presence of salt concentrations, temperatures, and other conditions which mimic normal physiological conditions. Oligonucleotides in the pool that bind to the ligand are retained on the column or bead, and nonbinding sequences are washed away. The oligonucleotides that bind the ligand are then amplified (after reverse transcription if RNA transcripts were utilized) by PCR (usually after elution). The selection process is repeated on the selected sequences for a total of about three to ten iterative rounds of the selection procedure. The resulting oligonucleotides are then amplified, cloned, and sequenced using standard procedures to identify the sequences of the oligonucleotides that are capable of binding the target ligand. Once an aptamer sequence has been identified, the aptamer may be further optimized by performing additional rounds of selection starting from a pool of oligonucleotides comprising a mutagenized aptamer sequence.

In vivo aptamer screening may be used following one or more rounds of in vitro selection (e.g., SELEX). For example, Konig, J. et al. (RNA. 2007, 13(4):614-622, incorporated herein by reference) describe combining SELEX and a yeast three-hybrid system for in vivo selection of aptamer.

Target Genes

The gene regulation cassette of the present invention is a platform that can be used to regulate the expression of any target gene that can be expressed in a target cell, tissue or organism. The term "target gene" refers to a polynucleotide that is introduced into a cell and is capable of being transcribed into RNA and translated and/or expressed under appropriate conditions. Alternatively, the target gene is endogenous to the target cell and the gene regulation cassette of the present invention is positioned into the target gene (for example into the 5' or 3' UTR of an endogenous target gene). An example of a target gene is a polynucleotide encoding a therapeutic polypeptide. In another embodiment, the target gene encodes an RNA such as a miRNA, rRNA, small or long noncoding RNAs, short hairpin RNA (shRNA) and any other regulatory RNAs. In one embodiment, the target gene is exogenous to the cell in which the recombinant DNA construct is to be transcribed. In another embodiment, the target gene is endogenous to the cell in which the recombinant DNA construct is to be transcribed.

The target gene according to the present invention may be a gene encoding a protein, or a sequence encoding a non-protein coding RNA. The target gene may be, for example, a gene encoding a structural protein, an enzyme, a cell signaling protein, a mitochondrial protein, a zinc finger protein, a hormone, a transport protein, a growth factor, a cytokine, an intracellular protein, an extracellular protein, a transmembrane protein, a cytoplasmic protein, a nuclear protein, a receptor molecule, an RNA binding protein, a DNA binding protein, a transcription factor, translational machinery, a channel protein, a motor protein, a cell adhesion molecule, a mitochondrial protein, a metabolic enzyme, a kinase, a phosphatase, exchange factors, a chaperone protein, and modulators of any of these. In embodiments, the target gene encodes erythropoietin (Epo), human growth hormone (hGH), transcription activator-like effector nucleases (TALEN), human insulin, CRISPR associated protein 9 (cas9), or an immunoglobulin (or portion thereof), including, e.g., a therapeutic antibody.

Expression Constructs

The present invention contemplates the use of a recombinant vector for introduction into target cells a polynucleotide encoding a target gene and containing the gene regulation cassette described herein. In many embodiments, the recombinant DNA construct of this invention includes additional DNA elements including DNA segments that provide for the replication of the DNA in a host cell and expression of the target gene in that cell at appropriate levels. The ordinarily skilled artisan appreciates that expression control sequences (promoters, enhancers, and the like) are selected based on their ability to promote expression of the target gene in the target cell. "Vector" means a recombinant plasmid, yeast artificial chromosome (YAC), mini chromosome, DNA mini-circle or virus (including virus derived sequences) that comprises a polynucleotide to be delivered into a host cell, either in vitro or in vivo. In one embodiment, the recombinant vector is a viral vector or a combination of multiple viral vectors.

Viral vectors for the aptamer-mediated expression of a target gene in a target cell, tissue, or organism are known in the art and include adenoviral (AV) vectors, adeno-associated virus (AAV) vectors, retroviral and lentiviral vectors, and Herpes simplex type 1 (HSV1) vectors.

Adenoviral vectors include, for example, those based on human adenovirus type 2 and human adenovirus type 5 that have been made replication defective through deletions in the E1 and E3 regions. The transcriptional cassette can be inserted into the E1 region, yielding a recombinant E1/E3-deleted AV vector. Adenoviral vectors also include helper-dependent high-capacity adenoviral vectors (also known as high-capacity, "gutless" or "gutted" vectors), which do not contain viral coding sequences. These vectors, contain the cis-acting elements needed for viral DNA replication and packaging, mainly the inverted terminal repeat sequences (ITR) and the packaging signal ($\Psi$). These helper-dependent AV vector genomes have the potential to carry from a few hundred base pairs up to approximately 36 kb of foreign DNA.

Recombinant adeno-associated virus "rAAV" vectors include any vector derived from any adeno-associated virus serotype, including, without limitation, AAV-1, AAV-2, AAV-3, AAV-4, AAV-5, AAV-7 and AAV-8, AAV-9, AAV-10, and the like. rAAV vectors can have one or more of the AAV wild-type genes deleted in whole or in part, preferably the Rep and/or Cap genes, but retain functional flanking ITR sequences. Functional ITR sequences are retained for the rescue, replication, packaging and potential chromosomal integration of the AAV genome. The ITRs need not be the wild-type nucleotide sequences, and may be altered (e.g., by the insertion, deletion or substitution of nucleotides) so long as the sequences provide for functional rescue, replication and packaging.

Alternatively, other systems such as lentiviral vectors can be used in embodiments of the invention. Lentiviral-based systems can transduce non-dividing as well as dividing cells making them useful for applications targeting, for examples, the non-dividing cells of the CNS. Lentiviral vectors are derived from the human immunodeficiency virus and, like that virus, integrate into the host genome providing the potential for long-term gene expression.

Polynucleotides, including plasmids, YACs, minichromosomes and minicircles, carrying the target gene containing the gene regulation cassette can also be introduced into a cell or organism by nonviral vector systems using, for example, cationic lipids, polymers, or both as carriers. Conjugated poly-L-lysine (PLL) polymer and polyethylenimine (PEI) polymer systems can also be used to deliver the vector to cells. Other methods for delivering the vector to cells includes hydrodynamic injection and electroporation and use of ultrasound, both for cell culture and for organisms. For a review of viral and non-viral delivery systems for gene delivery see Nayerossadat, N. et al. (Adv Biomed Res. 2012; 1:27) incorporated herein by reference.

Methods of Modulating Expression of a Target Gene

In one aspect, this invention provides a method of modulating expression of a target gene (e.g., a therapeutic gene), by (a) inserting the gene regulation polynucleotide cassette of the present invention into a target gene; (b) introducing the target gene comprising the gene regulation cassette into a cell; and (c) exposing the cell to a ligand that binds the aptamer in an effective amount to modulate target gene expression. In one embodiment, the polynucleotide cassette comprises an off riboswitch and exposure to the aptamer ligand reduces target gene expression. In one embodiment, the polynucleotide cassette comprises an on riboswitch and exposure to the aptamer ligand increases target gene expression. In one embodiment, the ligand is a small molecule. In aspects, expression of the target gene in target cells confers a desired property to a cell into which it was introduced, or otherwise leads to a desired therapeutic outcome.

In one embodiment, one or more gene regulation cassettes are inserted into the 3' UTR and/or the 5' UTR of the target gene. In one embodiment, a single gene regulation cassette is inserted into the 3' UTR of a target gene. In other embodiments 2, 3, 4, or more gene regulation cassettes are inserted in the target gene. In one embodiment, two gene regulation cassettes are inserted into the target gene. When multiple gene regulation cassettes are inserted into a target gene, they each can contain the same aptamer such that a single ligand can be used to modulate ribonuclease cleavage of the multiple cassettes and thereby modulate target gene expression. In other embodiments, multiple gene regulation cassettes are inserted into a target gene, each can contain a different aptamer so that exposure to multiple different small molecule ligands modulates target gene expression. In other embodiments, multiple gene regulation cassettes are inserted into a target gene, each containing different ribonuclease substrate sequences. This may be useful in reducing recombination and improving ease of incorporation into viral vectors.

In one embodiment, a polynucleotide cassette of the present invention is effective at modulating target gene expression when placed downstream (i.e., 3') of the target gene start codon. In one embodiment, when the polynucleotide cassette is inserted downstream of the translation start codon of the target gene, the on riboswitch is adjacent to the start codon. In other embodiments, the riboswitch is about 1 to about 100, about 1 to about 50, or about 1 to about 20 nucleotides from the start codon of the target gene. In one embodiment, the polynucleotide cassette comprises a 2A peptide sequence between the 3' end of the riboswitch and the target gene coding sequence. In one embodiment, the polynucleotide cassette comprises a 2A peptide sequence and a linker ("2A linker") between the 3' end of the riboswitch and the target gene coding sequence. The 2A sequence used in the Examples was identified from Thoseaasigna virus, therefore it is sometimes called "T2A." In place of T2A, other sequences that separate leader poly peptides from the remaining gene product may be used. Other 2A peptides include those identified in Picornaviruses: foot-and-mouth disease virus (F2A, the first one discovered), equine rhinitis A virus (E2A), and porcine teschovirus (P2A). Other 2A peptides include the 2A peptide from type C rotaviruses.

The polynucleotide cassette of the present invention can be used in combination with other mechanisms for the regulation of expression of the target gene. In one embodiment, a polynucleotide cassette of the present invention is used in combination with a gene regulation cassette that modulates target gene expression by aptamer-mediated regulation of alternative splicing as described in WO 2016/126747, incorporated herein by reference.

Methods of Treatment and Pharmaceutical Compositions

One aspect of the invention provides a method of regulating the level of a therapeutic protein delivered by gene therapy. In this embodiment, the "target gene" may encode the therapeutic protein. The "target gene" may encode a protein that is endogenous or exogenous to the cell.

The therapeutic gene sequence containing the regulatory cassette with aptamer-driven riboswitch is delivered to target cells in vitro or ex vivo, e.g., by a vector. The cell specificity of the "target gene" may be controlled by promoter or other elements within the vector. Delivery of the vector construct containing the target gene and the polynucleotide cassette, and the transfection of the target tissues resulting in stable transfection of the regulated target gene, is the first step in producing the therapeutic protein.

However, due to the presence of the regulatory cassette within the target gene sequence, the target gene is not expressed at significant levels. In some embodiments, the target gene is in the "off state" in the absence of the specific ligand that binds to the aptamer contained within in the regulatory cassette riboswitch. Only when the aptamer specific ligand is administered (or otherwise present in sufficient quantities) is the target gene expression activated. In other embodiments, the target gene is in the "off state" in the presence of the specific ligand that binds to the aptamer contained within in the regulatory cassette riboswitch. When administration stops (or the ligand is otherwise present at sufficiently low levels), target gene expression will occur.

The delivery of the vector construct containing the target gene and the delivery of the activating ligand generally are separated in time. The delivery of the activating ligand will control when the target gene is expressed, as well as the level of protein expression. The ligand may be delivered by a number of routes including, but not limited to, oral, intramuscular (IM), intravenous (IV), intraocular, or topically.

The timing of delivery of the ligand will depend on the requirement for activation of the target gene. For example, if the therapeutic protein encoded by the target gene is required constantly, in the case of the "on" riboswitches, an oral small molecule ligand may be delivered daily, or multiple times a day, to ensure continual activation of the target gene, and thus continual expression of the therapeutic protein. If the target gene has a long acting effect, the inducing ligand may be dosed less frequently.

This invention allows the expression of the therapeutic transgene to be controlled temporally, in a manner determined by the temporal dosing of the ligand specific to the aptamer within the riboswitch of the regulatory polynucleotide cassette. The increased expression of the therapeutic transgene only on ligand administration (in the case of the "on" riboswitches), increases the safety of a gene therapy treatment by allowing the target gene to be off in the absence of the ligand.

Different aptamers can be used to allow different ligands to activate target genes or repress target genes. In certain embodiments of the invention, each therapeutic gene containing a regulatory cassette will have a specific aptamer within the cassette that will be activated by a specific small molecule. This means that each therapeutic gene can be activated only by the ligand specific to the aptamer housed within it. In these embodiments, each ligand will only activate one therapeutic gene. This allows for the possibility that several different "target genes" may be delivered to one individual and each will be activated on delivery of the specific ligand for the aptamer contained within the regulatory cassette housed in each target gene.

This invention allows any therapeutic protein whose gene can be delivered to the body (such as erythropoietin (EPO) or a therapeutic antibody) to be produced by the body when the activating ligand is delivered. This method of therapeutic protein delivery may replace the manufacture of such therapeutic proteins outside of the body which are then injected or infused, e.g., antibodies used in cancer or to block inflammatory or autoimmune disease. The body containing the regulated target gene becomes the biologics manufacturing factory, which is switched on when the gene-specific ligand is administered.

Dosing levels and timing of dosing of a therapeutic protein may be important to therapeutic effect. For example, in the delivery of AVASTIN (anti-VEGF antibody) for cancer. The present invention increases the ease of dosing in response to monitoring for therapeutic protein levels and effects.

In one embodiment, the target gene may encode a nuclease that can target and edit a particular DNA sequence. Such nucleases include Cas9, zinc finger containing nucleases, or TALENs. In the case of these nucleases, the nuclease protein may be required for only a short period of time that is sufficient to edit the target endogenous genes. However, if an unregulated nuclease gene is delivered to the body, this protein may be present for the rest of the life of the cell. In the case of nucleases, there is an increasing risk of off-target editing the longer the nuclease is present. Regulation of expression of such proteins has a significant safety advantage. In this case, vector containing the nuclease target gene containing a regulatory cassette could be delivered to the appropriate cells in the body. The target gene is in the "off" state in the absence of the cassette-specific ligand, so no nuclease is produced. Only when the activating ligand is administered, is the nuclease produced. When sufficient time has elapsed allowing sufficient editing to occur, the ligand will be withdrawn and not administered again. Thus, the nuclease gene is thereafter in the "off" state and no further nuclease is produced and editing stops. This approach may be used to correct genetic conditions, including a number of inherited retinopathies such as LCA10 caused by mutations in CEP290 and Stargardt's Disease caused by mutations in ABCA4.

Administration of a regulated target gene encoding a therapeutic protein which is activated only on specific ligand administration may be used to regulate therapeutic genes to treat many different types of diseases, e.g., cancer with therapeutic antibodies, immune disorders with immune modulatory proteins or antibodies, metabolic diseases, rare diseases such as PNH with anti-C5 antibodies or antibody fragments as the regulated gene, or ocular angiogenesis with therapeutic antibodies, and dry AMD with immune modulatory proteins.

A wide variety of specific target genes, allowing for the treatment of a wide variety of specific diseases and conditions, are suitable for use in the present invention. For example, insulin or an insulin analog (preferably human insulin or an analog of human insulin) may be used as the target gene to treat type I diabetes, type II diabetes, or metabolic syndrome; human growth hormone may be used as the target gene to treat children with growth disorders or growth hormone-deficient adults; erythropoietin (preferably human erythropoietin) may be used as the target gene to treat anemia due to chronic kidney disease, anemia due to myelodysplasia, or anemia due to cancer chemotherapy.

The present invention may be especially suitable for treating diseases caused by single gene defects such as cystic fibrosis, hemophilia, muscular dystrophy, thalassemia, or sickle cell anemia. Thus, human β-, γ-, δ-, or ζ-globin may be used as the target gene to treat β-thalassemia or sickle cell anemia; human Factor VIII or Factor IX may be used as the target gene to treat hemophilia A or hemophilia B.

The ligands used in the present invention are generally combined with one or more pharmaceutically acceptable carriers to form pharmaceutical compositions suitable for administration to a patient. Pharmaceutically acceptable carriers include solvents, binders, diluents, disintegrants, lubricants, dispersion media, coatings, antibacterial and antifungal agents, isotonic and absorption delaying agents, and the like, generally used in the pharmaceutical arts. Pharmaceutical compositions may be in the form of tablets, pills, capsules, troches, and the like, and are formulated to be compatible with their intended route of administration. Examples of routes of administration include parenteral, e.g., intravenous, intradermal, intranasal, subcutaneous, oral, inhalation, transdermal (topical), transmucosal, and rectal.

The pharmaceutical compositions comprising ligands are administered to a patient in a dosing schedule such that an amount of ligand sufficient to desirably regulate the target gene is delivered to the patient. When the ligand is a small molecule and the dosage form is a tablet, capsule, or the like, preferably the pharmaceutical composition comprises from 0.1 mg to 10 g of ligand; from 0.5 mg to 5 g of ligand; from 1 mg to 1 g of ligand; from 2 mg to 750 mg of ligand; from 5 mg to 500 mg of ligand; or from 10 mg to 250 mg of ligand.

The pharmaceutical compositions may be dosed once per day or multiple times per day (e.g., 2, 3, 4, 5, or more times per day). Alternatively, pharmaceutical compositions may be dosed less often than once per day, e.g., once every 2, 3, 4, 5, 6, 7, 8, 9, 10, 11, 12, 13, or 14 days, or once a month or once every few months. In some embodiments of the invention, the pharmaceutical compositions may be administered to a patient only a small number of times, e.g., once, twice, three times, etc.

The present invention provides a method of treating a patient in need of increased expression of a therapeutic protein encoded by a target gene, the method comprising administering to the patient a pharmaceutical composition comprising a ligand for an aptamer, where the patient previously had been administered a recombinant DNA comprising the target gene, where the target gene contains a gene regulation cassette of the present invention that provides the ability to regulate expression of the target gene by the ligand of the aptamer by alternative splicing of pre-mRNA of the target gene, thereby increasing expression of the therapeutic protein.

Articles of Manufacture and Kits

Also provided are kits or articles of manufacture for use in the methods described herein. In aspects, the kits comprise the compositions described herein (e.g., for compositions for delivery of a vector comprising the target gene containing the gene regulation cassette) in suitable packaging. Suitable packaging for compositions (such as ocular compositions for injection) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing the administration, including e.g., any methods described herein. For example, in some embodiments, the kit comprises rAAV for expression of the target gene comprising the gene regulation cassette of the present invention, a pharmaceutically acceptable carrier suitable for injection, and one or more of: a buffer, a diluent, a filter, a needle, a syringe, and a package insert with instructions for performing the injections. In some embodiments, the kit is suitable for intraocular injection, intramuscular injection, intravenous injection and the like.

"Homology" and "homologous" as used herein refer to the percent of identity between two polynucleotide sequences or between two polypeptide sequences. The correspondence between one sequence to another can be determined by techniques known in the art. For example, homology can be determined by a direct comparison of two polypeptide molecules by aligning the sequence information and using readily available computer programs. Two polynucleotide or two polypeptide sequences are "substantially homologous" to each other when, after optimally aligned with appropriate insertions or deletions, at least about 80%, at least about 85%, at least about 90%, and at least about 95% of the nucleotides or amino acids, respectively, match over a defined length of the molecules, as determined using the methods above.

"Percent sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity. Alignment for purposes of determining percent amino acid or nucleic acid sequence identity can be achieved in ways known to the ordinarily-skilled artisan, for example, using publicly available computer software programs including BLAST, BLAST-2, ALIGN or Megalign (DNASTAR) software.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

"Heterologous" or "exogenous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The below table contains a listing of the DNA sequences of the constructs described herein as well as other sequences as described. The ribozyme sequence is in underlined, italicized lower case letters; the additional 3 base pair stem (3HP) is in double underlined lower case letters; the aptamer sequences are in wave underlined lower case letters; the stem sequences shared between twister stem and aptamer stem are grey shaded lower case letters; and the linker2A sequence is in thick underlined lower case letters; the coding sequences are in upper case letters.

| SEQ ID NO.: | Description | Sequence |
|---|---|---|
| 1 | wasp-twister in pEGFP-C1 | GTGACCGCCGCCGGGATCACTCTCGGCATGGACGAGC TGTACAAGTAAaccgcgg cttgtaatgcggccgtgtaaataatttacacgtcg gtctcaagcccgataaacgcagagagcaaggcggccgccataccacatttgtaga ggttttacttgctttaaaaaacctcccacacctcccctgaacctgaaacataaaatgaat gc |
| 2 | es-twister in pEGFPC1 | GTGACCGCCGCCGGGATCACTCTCGGCATGGACGAG CTGTACAAGTAAaccgc ggcaataaagcggttacaagcccgcaaaaat agcagagtaatgtcgcgatagcgcggcattaatgcagctttattggcggccgccata ccacatttgtagaggttttacttgctttaaaaaacctcccacacctcccctgaacctgaa acataaaatgaatgc |
| 3 | wasp-twister-mut in pEGFP-C1 | GTGACCGCCGCCGGGATCACTCTCGGCATGGACGAG CTGTACAAGTAAaccgcgg cttgtaatgcggccgtgtaaataatttacac gtcggtctcaagcccgataaacgcagagagcaagGCGGCCGCCATAC CACATTTGTAGAGGTTTTACTTGCTTTAAAAAACCTC CCACACCTCCCCCTGAACCTGAAACATAAAATGAAT GC |
| 4 | wasp_no Sac 0HP in pEGFP-C1 | GTGACCGCCGCCGGGATCACTCTCGGCATGGACGAG CTGTACAAGTAAa cttgtaatgcggccgtgtaaataatttacacgtcggtct caagcccgataaacgcagagagcaaggcggccgccataccacatttgtagaggttt tacttgctttaaaaaacctcccacacctcccctgaacctgaaacataaaatgaatgc |
| 5 | wasp_no Sac 3HP in pEGFP-C1 | GTGACCGCCGCCGGGATCACTCTCGGCATGGACGAG CTGTACAAGTAAa cgccttgtaatgcggccgtgtaaataatttacacgtcg gtctcaagcccgataaacgcagagagcaaggcggccgccataccacatttgtaga ggttttacttgctttaaaaaacctcccacacctcccctgaacctgaaacataaaatgaat gc |
| 6 | wasp_No Sac 0HP in pLuc | TCAGAGAGATCCTCATAAAGGCCAAGAAGGGCGGA AAGATCGCCGTGTAAa cttgtaatgcggccgtgtaaataatttacacgt cggtctcaagcccgataaacgcagagagcaaggcggccgccataccacatttgta gaggttttacttgctttaaaaaacctcccacacctcccctgaacctgaaacataaaatg aatg |
| 7 | wasp_No Sac 3HP in pLuc | TCAGAGAGATCCTCATAAAGGCCAAGAAGGGCGGA AAGATCGCCGTGTAAa cgccttgtaatgcggccgtgtaaataatttaca |

-continued

| SEQ ID NO.: | Description | Sequence |
|---|---|---|
| | | *cgtcggtctcaagcccgataaacgcagagagcaaggcg*gccgccataccacattt gtagaggttttacttgctttaaaaaacctcccacacctcccctgaacctgaaacataaa atgaatgc |
| 8 | waspGua1 in pLuc | TCAGAGAGATCCTCATAAAGGCCAAGAAGGGCGGA AAGATCGCCGTGTAAa *cgccttgtaatgcggccgtgtaaat*cactcatat aatcgcgtggatatggcacgcaagtttctaccgggcaccgtaaatgtccgactatgggt *gatttacacgtcggtctcaagcccgataaacgcagagagcaaggcg*gccgccata ccacatttgtagaggttttacttgctttaaaaaacctcccacacctcccctgaacctgaa acataaaatgaatgc |
| 9 | waspGua2 in pLuc | TCAGAGAGATCCTCATAAAGGCCAAGAAGGGCGGA AAGATCGCCGTGTAAa *cgccttgtaatgcggccgtgtaaa*actcatata atcgcgtggatatggcacgcaagtttctaccgggcaccgtaaatgtccgactatggt*t ttacacgtcggtctcaagcccgataaacgcagagagcaaggcg*gcggccgccatacca catttgtagaggttttacttgctttaaaaaacctcccacacctcccctgaacctgaaaca taaaatgaatgc |
| 10 | waspGua3 in pLuc | TCAGAGAGATCCTCATAAAGGCCAAGAAGGGCGGA AAGATCGCCGTGTAAa *cgccttgtaatgcggccgtgtaa*ctcataatc gcgtggatatggcacgcaagtttctaccgggcaccgtaaatgtccgactatggg*ttac acgtcggtctcaagcccgataaacgcagagagcaaggcg*gccgccataccacatt tgtagaggttttacttgctttaaaaaacctcccacacctcccctgaacctgaaacataaa atgaatgc |
| 11 | waspGua4 in pLuc | TCAGAGAGATCCTCATAAAGGCCAAGAAGGGCGGA AAGATCGCCGTGTAAa *cgccttgtaatgcggccgtgta*tcatataatcgc gtggatatggcacgcaagtttctaccgggcaccgtaaatgtccgactatgg*tacacgtc ggtctcaagcccgataaacgcagagagcaaggcg*gccgccataccacatttgtag aggttttacttgctttaaaaaacctcccacacctcccctgaacctgaaacataaaatga atgc |
| 12 | waspGua5 in pLuc | TCAGAGAGATCCTCATAAAGGCCAAGAAGGGCGGA AAGATCGCCGTGTAAa *cgccttgtaatgcggccgtgtt*catataatcgcg tggatatggcacgcaagtttctaccgggcaccgtaaatgtccgactatg*acacgtcg gtctcaagcccgataaacgcagagagcaaggcg*gccgccataccacatttgtaga ggttttacttgctttaaaaaacctcccacacctcccctgaacctgaaacataaaatgaat gc |
| 13 | waspGua6 in pLuc | TCAGAGAGATCCTCATAAAGGCCAAGAAGGGCGGA AAGATCGCCGTGTAAa *cgccttgtaatgcggccgtgt*catataatcgcgt ggatatggcacgcaagtttctaccgggcaccgtaaatgtccgactatg*acacgtcgg t ctcaagcccgataaacgcagagagcaaggcg*gccgccataccacatttgtagagg ttttacttgctttaaaaaacctcccacacctcccctgaacctgaaacataaaatgaatgc |
| 14 | waspGua7 in pLuc | TCAGAGAGATCCTCATAAAGGCCAAGAAGGGCGGA AAGATCGCCGTGTAAa *cgccttgtaatgcggccgtg*catataatcgcgt ggatatggcacgcaagtttctaccgggcaccgtaaatgtccgactatg*cacgtcggtct caagcccgataaacgcagagagcaaggcg*gccgccataccacatttgtagaggttt tacttgctttaaaaaacctcccacacctcccctgaacctgaaacataaaatgaatgc |
| 15 | waspGua8 in pLuc | TCAGAGAGATCCTCATAAAGGCCAAGAAGGGCGGA AAGATCGCCGTGTAAa *cgccttgtaatgcggccgtg*atataatcgcgtg gatatggcacgcaagtttctaccgggcaccgtaaatgtccgactat*cacgtcggtctca agcccgataaacgcagagagcaaggcg*gccgccataccacatttgtagaggttta cttgctttaaaaaacctcccacacctcccctgaacctgaaacataaaatgaatgc |
| 16 | waspGua9 in pLuc | TCAGAGAGATCCTCATAAAGGCCAAGAAGGGCGGA AAGATCGCCGTGTAAa *cgccttgtaatgcggccgt*atataatcgcgtgg atatggcacgcaagtttctaccgggcaccgtaaatgtccgactat*acgtcggtctcaag cccgataaacgcagagagcaaggcg*gccgccataccacatttgtagaggttttactt gctttaaaaaacctcccacacctcccctgaacctgaaacataaaatgaatgc |
| 17 | waspGua12 in pLuc | TCAGAGAGATCCTCATAAAGGCCAAGAAGGGCGGA AAGATCGCCGTGTAAa *cgccttgtaatgcggccg*ataatcgcgtggata tggcacgcaagtttctaccgggcaccgtaaatgtccgact*cgtcggtctcaagcccga taaacgcagagagcaaggcg*gccgccataccacatttgtagaggttttacttgcttta aaaaacctcccacacctcccctgaacctgaaacataaaatgaatgc |
| 18 | waspGua13 in pLuc | TCAGAGAGATCCTCATAAAGGCCAAGAAGGGCGGA AAGATCGCCGTGTAAa *cgccttgtaatgcggcc*ataatcgcgtggatat ggcacgcaagtttctaccgggcaccgtaaatgtccgact*gtcggtctcaagcccgata aacgcagagagcaaggcg*gccgccataccacatttgtagaggttttacttgctttaaa aaacctcccacacctcccctgaacctgaaacataaaatgaatgc |

| SEQ ID NO.: | Description | Sequence |
|---|---|---|
| 19 | waspGua14 in pLuc | TCAGAGAGATCCTCATAAAGGCCAAGAAGGGCGGA<br>AAGATCGCCGTGTAAa cgccttgtaatgcggcctaatcgcgtggatatg<br>gcacgcaagtttctaccgggcaccgtaaatgtccgacgtcggtctcaagcccgataa<br>acgcagagagcaaggcggccgccataccacatttgtagaggttttacttgctttaaaa<br>aacctcccacacctcccctgaacctgaaacataaaatgaatgc |
| 20 | waspGua15 in pLuc | TCAGAGAGATCCTCATAAAGGCCAAGAAGGGCGGA<br>AAGATCGCCGTGTAAa cgccttgtaatgcggccatataatcgcgtggat<br>atggcacgcaagtttctaccgggcaccgtaaatgtccgactatgtcggtctcaagccc<br>gataaacgcagagagcaaggcggccgccataccacatttgtagaggttttacttgctt<br>taaaaaacctcccacacctcccctgaacctgaaacataaaatgaatgc |
| 21 | waspGua16 in pLuc | TCAGAGAGATCCTCATAAAGGCCAAGAAGGGCGGA<br>AAGATCGCCGTGTAAa cgccttgtaatgcggcatataatcgcgtggatat<br>ggcacgcaagtttctaccgggcaccgtaaatgtccgactattcggtctcaagcccgat<br>aaacgcagagagcaaggcggccgccataccacatttgtagaggttttacttgctttaa<br>aaaacctcccacacctcccctgaacctgaaacataaaatgaatgc |
| 22 | waspGua17 in pLuc | TCAGAGAGATCCTCATAAAGGCCAAGAAGGGCGGA<br>AAGATCGCCGTGTAAa cgccttgtaatgcggctataatcgcgtggatatg<br>gcacgcaagtttctaccgggcaccgtaaatgtccgactatcggtctcaagcccgataa<br>acgcagagagcaaggcggccgccataccacatttgtagaggttttacttgctttaaaa<br>aacctcccacacctcccctgaacctgaaacataaaatgaatgc |
| 23 | waspGua18 in pLuc | TCAGAGAGATCCTCATAAAGGCCAAGAAGGGCGGA<br>AAGATCGCCGTGTAAa cgccttgtaatgcggccgtgtataatcgcgtgg<br>atatggcacgcaagtttctaccgggcaccgtaaatgtccgactacacgtcggtctcaa<br>gcccgataaacgcagagagcaaggcggccgccataccacatttgtagaggttttact<br>tgctttaaaaaacctcccacacctcccctgaacctgaaacataaaatgaatgc |
| 24 | waspGua19 in pLuc | TCAGAGAGATCCTCATAAAGGCCAAGAAGGGCGGA<br>AAGATCGCCGTGTAAa cgccttgtaatgcggccgttataatcgcgtggat<br>atggcacgcaagtttctaccgggcaccgtaaatgtccgactaacgtcggtctcaagcc<br>cgataaacgcagagagcaaggcggccgccataccacatttgtagaggttttacttgc<br>tttaaaaaacctcccacacctcccctgaacctgaaacataaaatgaatgc |
| 25 | waspGua20 in pLuc | TCAGAGAGATCCTCATAAAGGCCAAGAAGGGCGGA<br>AAGATCGCCGTGTAAa cgccttgtaatgcggccgtataatcgcgtggat<br>atggcacgcaagtttctaccgggcaccgtaaatgtccgactacgtcggtctcaagccc<br>gataaacgcagagagcaaggcggccgccataccacatttgtagaggttttacttgctt<br>taaaaaacctcccacacctcccctgaacctgaaacataaaatgaatgc |
| 26 | Epo-waspGua16 | GCTGTACACGGGAGAGGTCTGCAGGAGAGGGGACA<br>GGTGAggatcca cgccttgtaatgcggcatataatcgcgtggatatggcacgcaa<br>gtttctaccgggcaccgtaaatgtccgactattcggtctcaagcccgataaacgcaga<br>gagcaaggcgctcgagggcccagatctaattcaccccaccagtgcaggctgcctatc<br>agaaagtggtggctggtgtggctaatgccctggcccacaagtatcactaagctcgcttt<br>cttgctgtccaatttctattaaaggttcctttt |
| 27 | Epo-mutwaspGua16 | GCTGTACACGGGAGAGGTCTGCAGGAGAGGGGACA<br>GGTGAggatcca cgccttgtgatgcggcatataatcgcgtggatatggcacgcaa<br>gtttctaccgggcaccgtaaatgtccgactattcggtctcaagcccgataaacgcaga<br>gagcaaggcgctcgagggcccagatctaattcaccccaccagtgcaggctgcctatc<br>agaaagtggtggctggtgtggctaatgccctggcccacaagtatcactaagctcgcttt<br>cttgctgtccaatttctattaaaggttcctttt |
| 28 | twister_theo_1 in pLuc | TCAGAGAGATCCTCATAAAGGCCAAGAAGGGCGGA<br>AAGATCGCCGTGTAAa cgccttgtaatgcggcatgataccagccgaaa<br>ggcccttggcagcattcggtctcaagcccgataaacgcagagagcaaggcggccg<br>ccataccacatttgtagaggttttacttgctttaaaaaacctcccacacctcccctgaac<br>ctgaaacataaaatgaatgc |
| 29 | twister_theo_2 in pLuc | TCAGAGAGATCCTCATAAAGGCCAAGAAGGGCGGA<br>AAGATCGCCGTGTAAa cgccttgtaatgcggcgacgataccagccgaa<br>gtctcggtctcaagcccgataaacgcagagagcaaggcggc<br>cgccataccacatttgtagaggttttacttgctttaaaaaacctcccacacctcccctga<br>acctgaaacataaaatgaatgc |
| 30 | twister_theo_3 in pLuc | TCAGAGAGATCCTCATAAAGGCCAAGAAGGGCGGA<br>AAGATCGCCGTGTAAa cgccttgtaatgcggcgcgataccagccgaa<br>ggcccttggcagcgttcggtctcaagcccgataaacgcagagagcaaggcggcc<br>gccataccacatttgtagaggttttacttgctttaaaaaacctcccacacctcccctgaa<br>cctgaaacataaaatgaatgc |

| SEQ ID NO.: | Description | Sequence |
|---|---|---|
| 31 | twister_theo_4 in pLuc | TCAGAGAGATCCTCATAAAGGCCAAGAAGGGCGGA AAGATCGCCGTGTAAa cgccttgtaatgcggcctgataccagccgaaa ggcccttggcagcgttcggtctcaagcccgataaacgcagagagcaaggcggcc gccataccacatttgtagaggttttacttgctttaaaaaacctcccacacctcccctgaa cctgaaacataaaatgaatgc |
| 32 | ATG_wtWaspGua16 in pLuc | ATGa cgccttgtaatgcggcatataatcgcgtggatatggcacgcaagtttctaccg ggcaccgtaaatgtccgactattcggtctcaagcccgataaacgcagagagcaagg cgaaggcggatcttcaggtagtggcgagggcagaggaagtcttctaacatgcggtga cgtggaggagaatcccggccccGAAGACGCCAAAAACATAAAG AAAGGCCCGGCGCCA |
| 33 | ATG_mutWaspGua16 in pLuc | ATGa cgccttgtgatgcggcatataatcgcgtggatatggcacgcaagtttctaccg ggcaccgtaaatgtccgactattcggtctcaagcccgataaacgcagagagcaagg cgaaggcggatcttcaggtagtggcgagggcagaggaagtcttctaacatgcggtga cgtggaggagaatcccggccccGAAGACGCCAAAAACATAAAG AAAGGCCCGGCGCCA |
| 34 | 10aa_wtWaspGua16 in pLuc | ATGGTGAGCAAGGGCGAGGAGCTGTTCACCa cgccttgta atgcggcatataatcgcgtggatatggcacgcaagtttctaccgggcaccgtaaatgtc cgactattcggtctcaagcccgataaacgcagagagcaaggcgaaggcggatcttc aggtagtggcgagggcagaggaagtcttctaacatgcggtgacgtggaggagaatc ccggccccGAAGACGCCAAAAACATAAAGAAAGGCCCG GCGCCA |
| 35 | 10aa_mutWaspGua16 in pLuc | ATGGTGAGCAAGGGCGAGGAGCTGTTCACCa cgccttgtg atgcggcatataatcgcgtggatatggcacgcaagtttctaccgggcaccgtaaatgtc cgactattcggtctcaagcccgataaacgcagagagcaaggcgaaggcggatcttc aggtagtggcgagggcagaggaagtcttctaacatgcggtgacgtggaggagaatc ccggccccGAAGACGCCAAAAACATAAAGAAAGGCCCG GCGCCA |
| 36 | GT_8bp in pLuc | TCAGAGAGATCCTCATAAAGGCCAAGAAGGGCGGA AAGATCGCCGTGTAAta ▓▓▓▓▓▓tataatcgcgtggatatggcacgcaa gtttctaccgggcaccgtaaatgtccgacta▓▓▓▓▓▓gtaatgcggccgtgtaaataat ttacacgtcggtctcaagcccgataaacgcagagagcaagcggccgccatacca catttgtagaggttttacttgctttaaaaaacctcccacacctcccctgaacctgaaaca taaatgaatgc |
| 37 | TG_9b in pLuc | TCAGAGAGATCCTCATAAAGGCCAAGAAGGGCGGA AAGATCGCCGTGTAAa cgccttgtaatgcggccgtgtaaataatttaca cgtcggtctcaagcccgataaacgcagagag▓▓▓▓▓▓tataatcgcgtggatatg gcacgcaagtttctaccgggcaccgtaaatgtccgacta▓▓▓▓▓▓ataccacatttgta gaggttttacttgctttaaaaaacctcccacacctcccctgaacctgaaacataaaatg aatgc |
| 38 | Twister ribozyme is from Nasonia vitripennis (wasp twister) | cttgtaatgcggccgtgtaaataatttacacgtcggtctcaagcccgataaacgcagag agcaag |
| 39 | Twister ribozyme is from an environmental sample (es twister) | ggcaataaagcggttacaagcccgcaaaaatagcagagtaatgtcgcgatagcgcg gcattaatgcagctttattg |

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

Example 1

Twister ribozymes self-cleave and suppress gene expression in mammalian cells

Experimental Procedures:

Plasmid constructs: oligonucleotides containing wild type or mutant twister ribozyme sequences, either from *Nasonia Vitripennis* (wasp) or from environmental samples, flanked by BsrGI and MfeI sites, were synthesized (IDT). The synthesized oligonucleotides ("oligos") were digested with BsrGI and MfeI and cloned into pEGFP-C1 (Clontech) digested with the compatible restriction enzymes. The sequences of the constructed vectors were verified by DNA sequencing (Genewiz).

Transfection and measurement of GFP fluorescence: $3.5 \times 10^4$ HEK 293 cells were plated in a 96-well flat bottom plate the day before transfection. Plasmid DNA (500 ng) was added to a tube or a 96-well U-bottom plate. Separately, TransIT-293 reagent (Mirus; 1.4 µl) was added to 50 µl Opti-mem I media (Life Technologies), and allowed to sit for 5 minutes at room temperature ("RT"). Then, 50 µl of this diluted transfection reagent was added to the DNA, mixed, and incubated at RT for 20 min. Finally, 7 µl of this solution was added to a well of cells in a 96-well plate. A LacZ construct that does not express GFP was used as background negative control. GFP fluorescence intensity was measured by Tecan plate reader, using Excitation wavelength at 484 nm, Emission wavelength at 510 nm and Excitation bandwidth at 5 nm. The GFP fluorescence intensity was expressed as the value generated by GFP constructs subtracted by the value generated by LacZ construct.

Figure 1B:
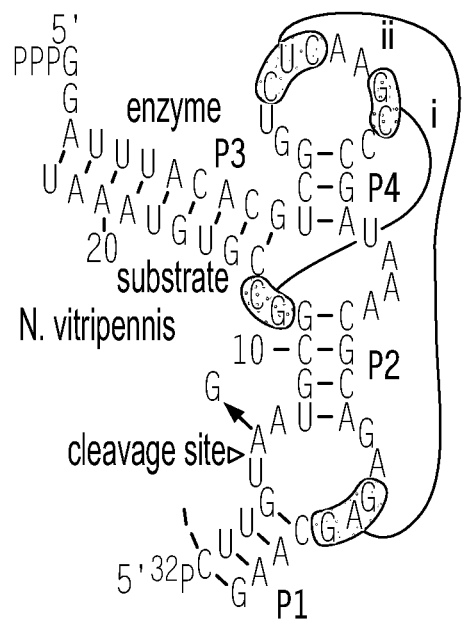
Figure 1B:
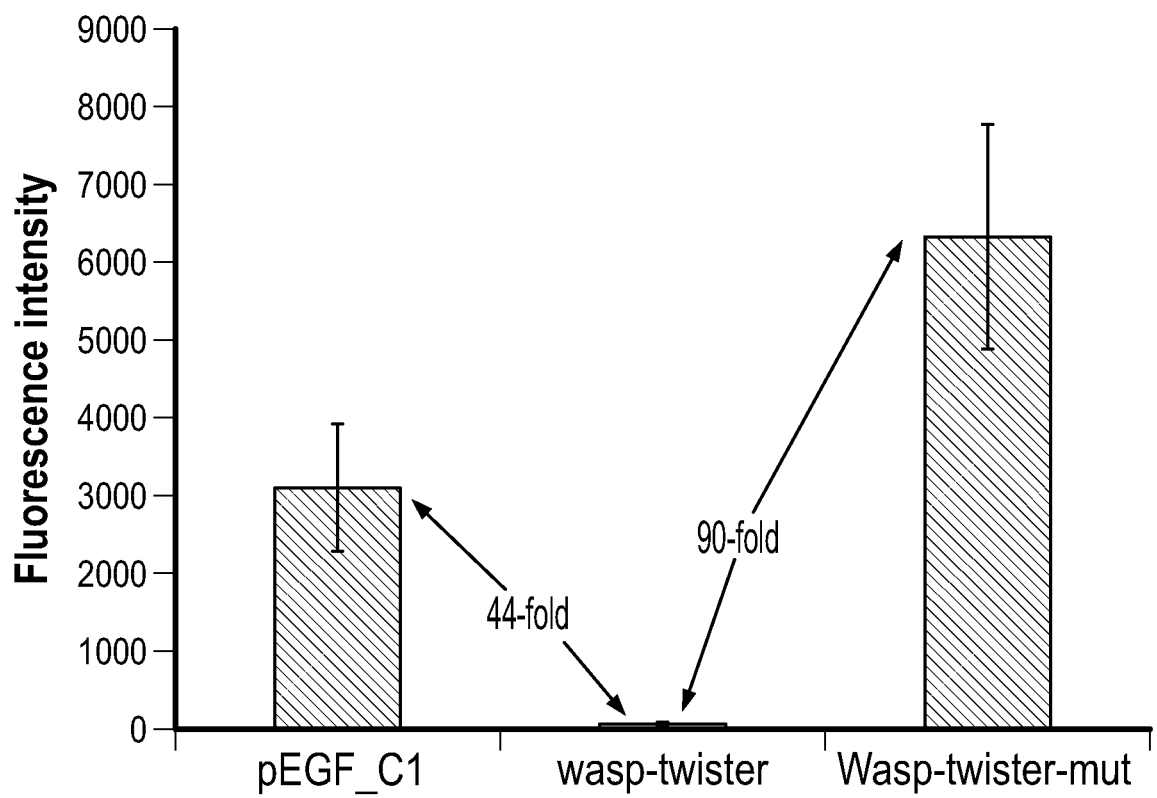

Results:

Twister ribozymes exist in many species of bacteria and eukarya. However, their self-cleaving activity in mammalian cells has not been determined. To investigate whether twister ribozyme could cleave mRNA and suppress gene expression in mammalian cells, the twister ribozyme sequence from *N. Vitripennis* (wasp) and twister ribozyme sequence from environmental samples was each inserted into the 3' UTRs of the EGFP gene in the pEGFP-C1 vector. As shown in FIG. 1a, insertion of wasp-twister ribozyme in the 3' UTR resulted in 97% and 36-fold inhibition of GFP expression when comparing with the pEGFP-C1 control construct. The twister sequence from environmental sample (es-twister) did not lead to as robust suppression of GFP expression as wasp-twister, generating about 50% suppression of GFP expression when comparing with the control GFP vector. To further determine that the suppression of GFP expression was due to the twister ribozyme cleavage, a mutant construct was generated where A6 was replaced with G, making twister ribozyme cleavage-incapable. This A6G mutation completely abolished the suppression in GFP expression, while the wild type twister ribozyme caused 44-fold reduction, as shown in FIG. 1b. These results indicate that in mammalian cells twister ribozymes self-cleave when present in the target gene RNA and thereby suppress target gene expression.

Example 2

Modification of Twister Ribozyme P1 Stem Sequence Improves Twister Ribozyme Cleavage Activity Experimental Procedures:

Plasmid constructs: The following primers were used to generate constructs GFP_wasp_No Sac 0HP or GFP_wasp_No Sac 3HP: forward primers NoSac_Fwd (5' GCTGTA-CAAGTAAACTTGTAATGCGGCCGTGTAAATAATT-TAC) and NoSac3HP_Fwd (5' AGCTGTA-CAAGTAAACGCCTTGTAATGCGGCCGTGTAAATAAT-TTAC) and reverse primer MfeI Rev (5' ACAACAACAATTGCATTCATTTTATG). GFP_wasp-twister vector was used as template and the PCR-amplified DNA fragments were digested with BsrGI and MfeI and cloned into pEGFP-C1 digested with BsrGI and MfeI enzymes. The EGFP gene in pEGFP-C1 was replaced with the firefly luciferase gene to generate the pFLuc vector using Gibson cloning strategy and cloning kit (NEB). The same strategy was used to generate constructs Luc_wasp_No Sac 0HP and Luc_wasp_No Sac 3 HP by replacing the EGFP gene in constructs GFP_wasp_no Sac 0HP and GFP_wasp_no Sac 3HP with the firefly luciferase gene.

Measurement of GFP fluorescence intensity was performed as described in Example 1.

Firefly luciferase assay of cultured cells: 24 hours after media change, plates were removed from the incubator, equilibrated to RT for several minutes on a lab bench, and then aspirated. Glo-lysis buffer (Promega, 100 µL, RT) was added, and the plates allowed to remain at RT for at least 5 minutes. The well contents were mixed by 50 µL trituration, and 20 µL of each sample was mixed with 20 µL of bright-glo reagent (Promega) that had been diluted to 10% in glo-lysis buffer. 96 wells were spaced on an opaque white 384-well plate. Following a 5-minute incubation at RT, luminescence was measured using a Tecan machine with 500 mSec read time. The luciferase activity was expressed as mean relative light unit (RLU)±S.D.

Figure 2A:
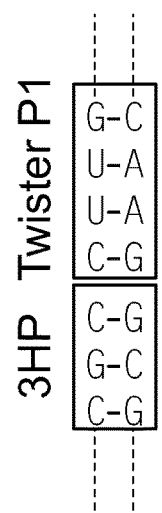
FIGS. 2a-2b. Modification of P1 stem sequence improves twister ribozyme cleavage activity.
Figure 2B:
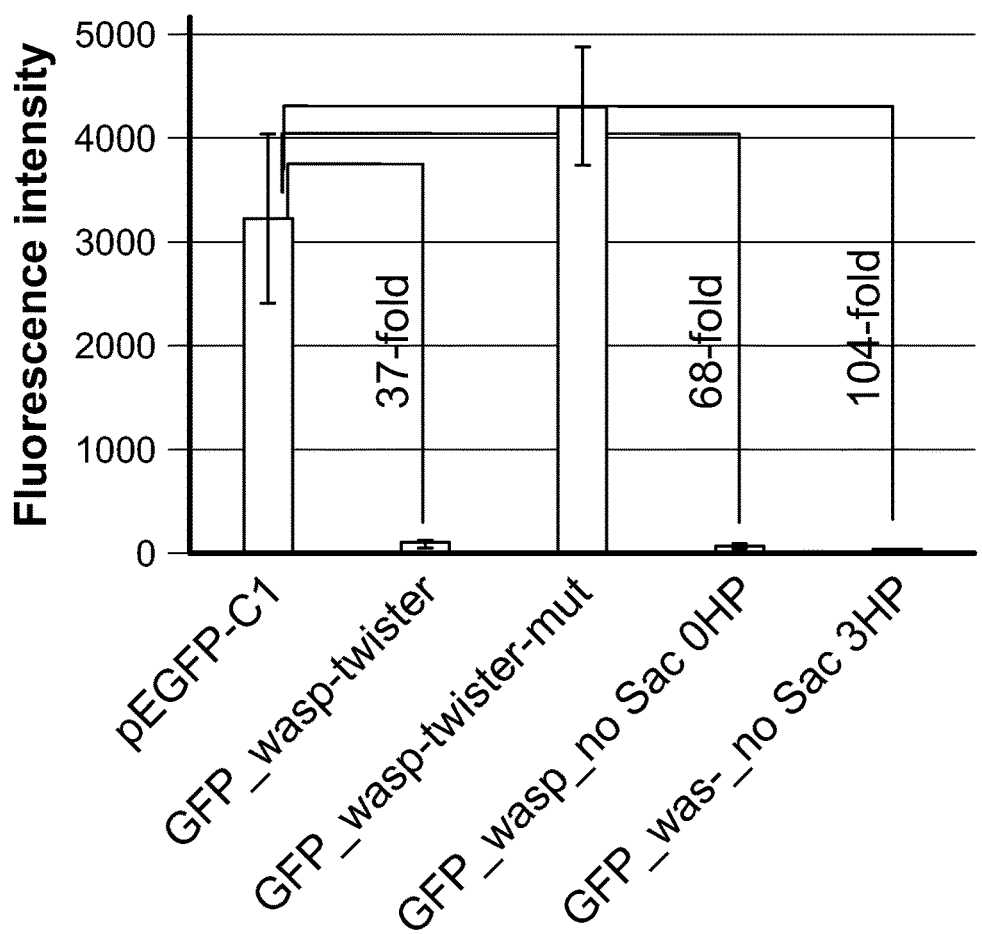
Figure 2C:
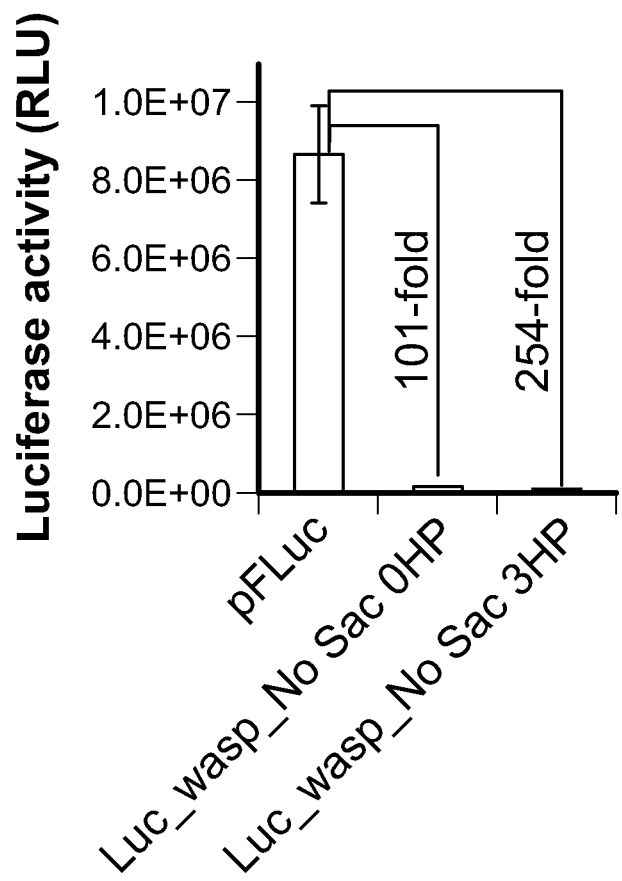
FIG. 2c. Shown is the result of luciferase assay. HEK 293 cells were transfected with the indicated constructs containing firefly luciferase gene and twister with or without 3HP in 3' UTR.

Results:

To further enhance the cleavage activity of the twister ribozyme in mammalian cells, and thereby increase the dynamic range of suppression of target gene expression by the ribozyme, the sequences adjacent to the twister P1 stem were modified in the GFP-twister construct. First, the SacII sequence located at the 5' end of the twister sequence was deleted, generating GFP_wasp_no Sac 0HP. To determine whether a longer P1 stem could stabilize the twister ribozyme and thus enhance its cleavage activity, the sequence of SacII site was replaced with CGC to create a 3 base pair stem (3HP) at the base of the P1 stem of the twister ribozyme (FIG. 2a), generating construct GFP_wasp_no Sac 3HP. Interestingly, as shown in FIG. 2b, deletion of SacII sequence increased the GFP suppression, from 37-fold by the construct with the SacII sequence to 68-fold by the construct GFP_wasp_no Sac 0HP without the SacII site, suggesting the SacII sequence adjacent to the 5' of the P1 sequence impaired the ribozyme activity. Addition of a 3 bp stem to the base of the P1 stem further enhanced the ribozyme activity, generating 104-fold suppression of GFP expression. The activity of this modified twister construct was also tested using firefly luciferase gene as a reporter. As shown in FIG. 2c, deletion of SacII sequence resulted in 101-fold reduction of luciferase activity when comparing to pFLuc control construct. Addition of a 3 bp stem at the P1 stem further enhanced the reduction of luciferase activity to 254 fold compared to the control construct.

Example 3

Use of Xpt-Guanine Aptamer to Regulate Target Gene Expression Via Modulating Twister Ribozyme Experimental Procedures:

Oligos containing the twister ribozyme sequence linked with an xpt-guanine aptamer were synthesized (IDT), and cloned into the pLuc vector using the Gibson cloning strategy and kit (NEB). Construct sequences were verified by DNA sequencing (Genewiz).

Transfection and aptamer ligand treatment: HEK 293 cells were transfected as described in Example 1. Four hours after transfection, the media was aspirated, and new media with or without 500 µM guanine or 1 mM guanosine (Sigma) was added. Luciferase assay was performed 20 to 24 hours after guanine or guanosine treatment as described in Example 2. The reduction fold was expressed as the quotient of luciferase activity obtained in the absence of aptamer ligand divided by the value obtained in the presence of the aptamer ligand.

ELISA assay for measuring mouse Epo in culture media: Supernatant was collected 18 hours after drug treatment, and an ELISA was performed using ELISA kit (R&D) according to manufacturer's instructions. The data was analyzed using 4-parameter curve fitting.

Results:

In order to regulate the cleavage activity of twister ribozyme, and thereby regulate target gene expression, aptamer sequence was linked to the P3 stem of the twister ribozyme. When aptamer ligand is not present, the structure of the ribozyme is disrupted, preventing cleavage, and allowing target gene expression (FIG. 3a, top panel). Addition of the aptamer ligand leads to a conformational change allowing twister ribozyme cleavage and reducing target gene expression (FIG. 3a, bottom panel). The P1 stem of the xpt-guanine aptamer was grafted to the P3 stem of twister ribozyme to generate guanine-responsive twister ribozyme. In this configuration (FIG. 3a), in the absence of aptamer ligand, insertion of aptamer sequence between the two arms of the twister P3 stem disrupts the P3 stem and the twister ribozyme structure, disrupting cleavage activity and allowing the target gene to be expressed. In the presence of aptamer ligand, aptamer/ligand binding brings together the arms of the stem, facilitating the P3 stem formation and twister cleavage activity, thereby suppressing target gene expression.

Figure 3B:
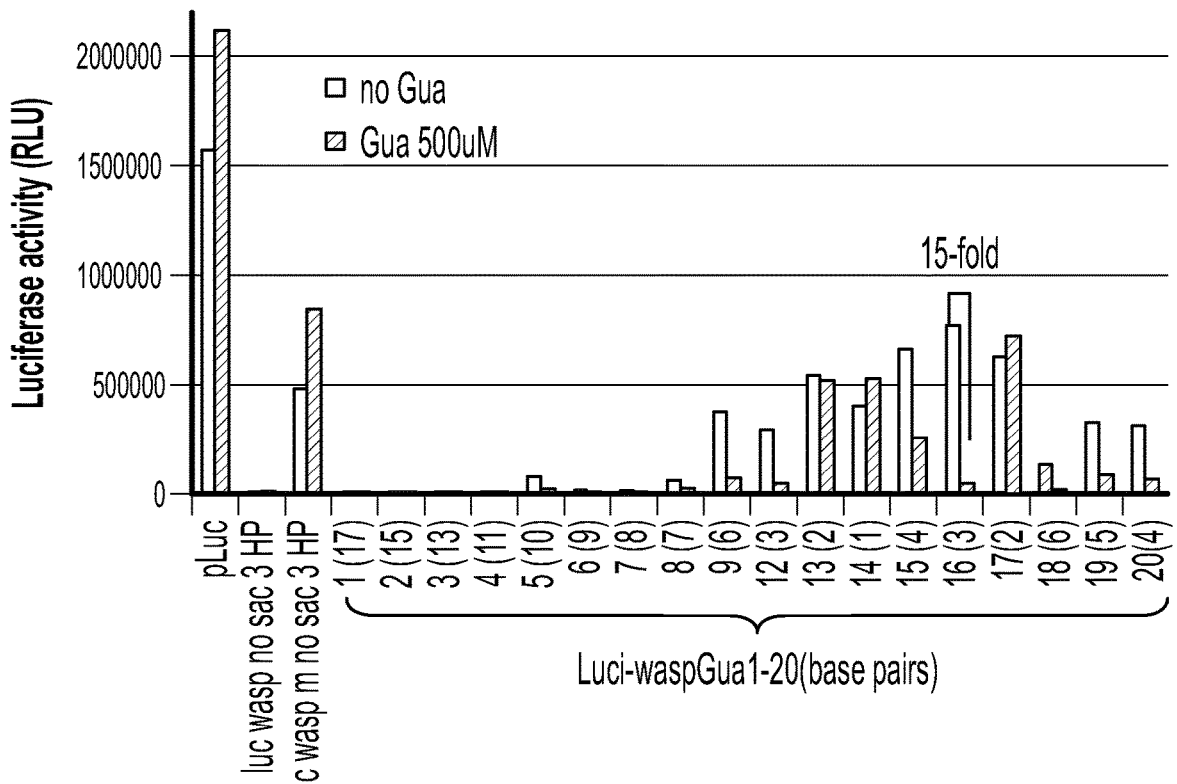

In addition, we speculated that if the length of the stem connecting the aptamer and twister is too long, the stem formation could be independent of the existence of aptamer sequence and occur in the absence of aptamer ligand. However, if the stem is too short, even in the presence of aptamer ligand, a stable stem structure may not be achieved. Therefore, to determine an optimal length of the stem (to achieve optimal responsiveness to aptamer ligand), the length of the stem connecting aptamer and ribozyme was optimized. We made serial truncations to the stem, generating a total of 20 constructs with the length of the stem ranging from 17 to 1 bp. As shown in the FIG. 3b, of all the 20 constructs constructed, Luci-waspGua16 which has 3 bp of stem connecting the guanine aptamer directly to twister loop 2, showed the most profound reduction in luciferase gene expression (15 fold). Constructs with stem length shorter than 3 bp or longer than 7 bp showed no significant reduction upon guanine treatment.

Figure 3C:
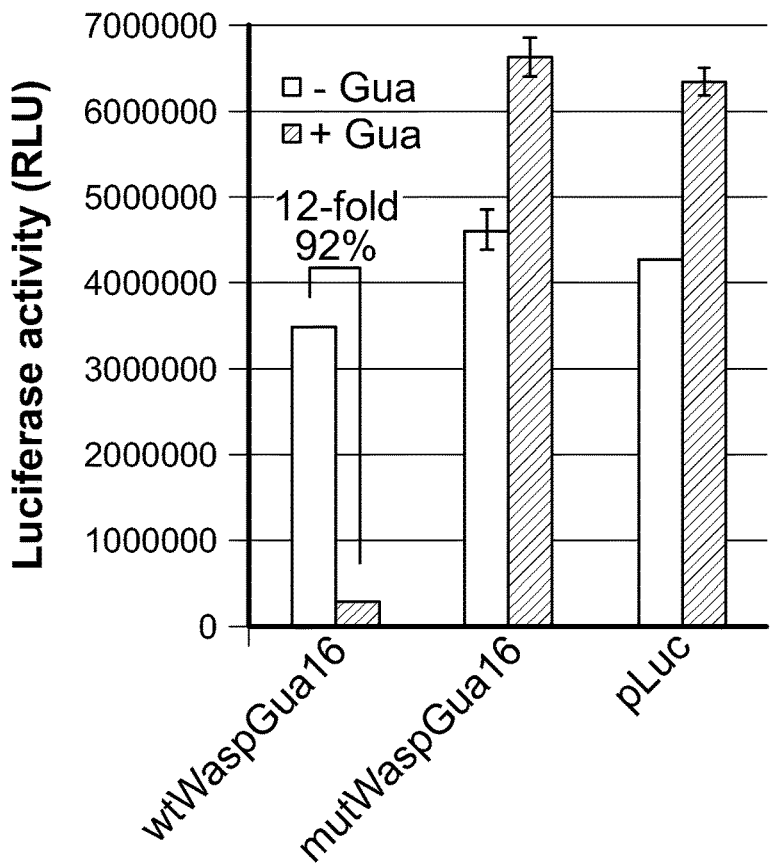
Figure 3D:
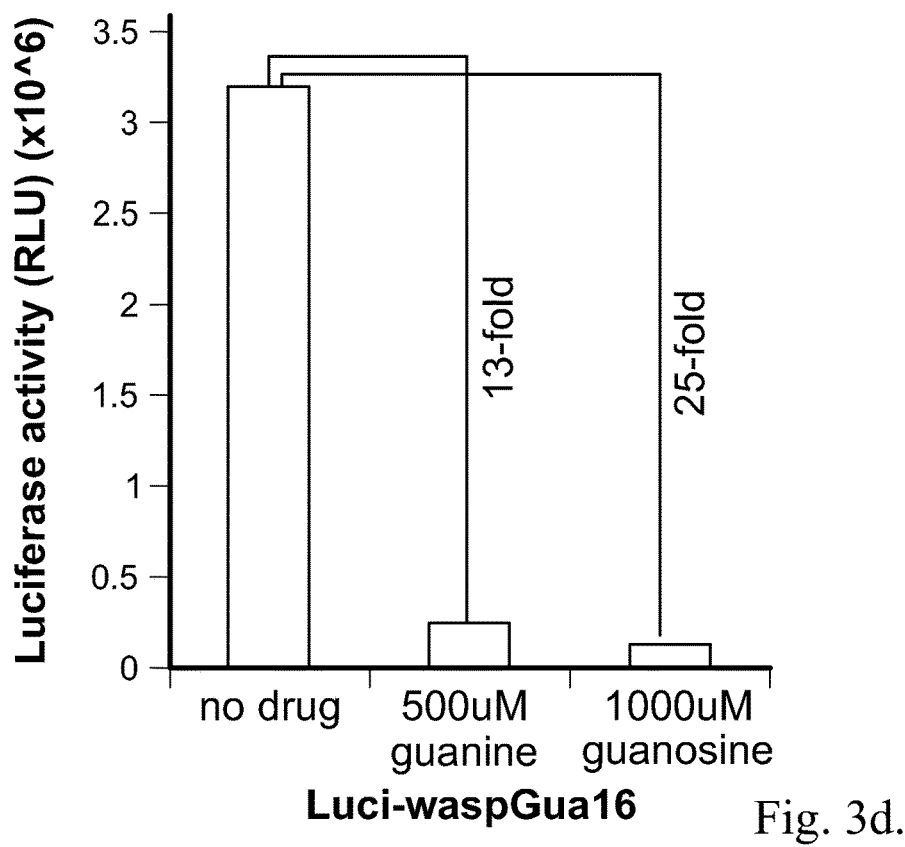
Figure 3E:
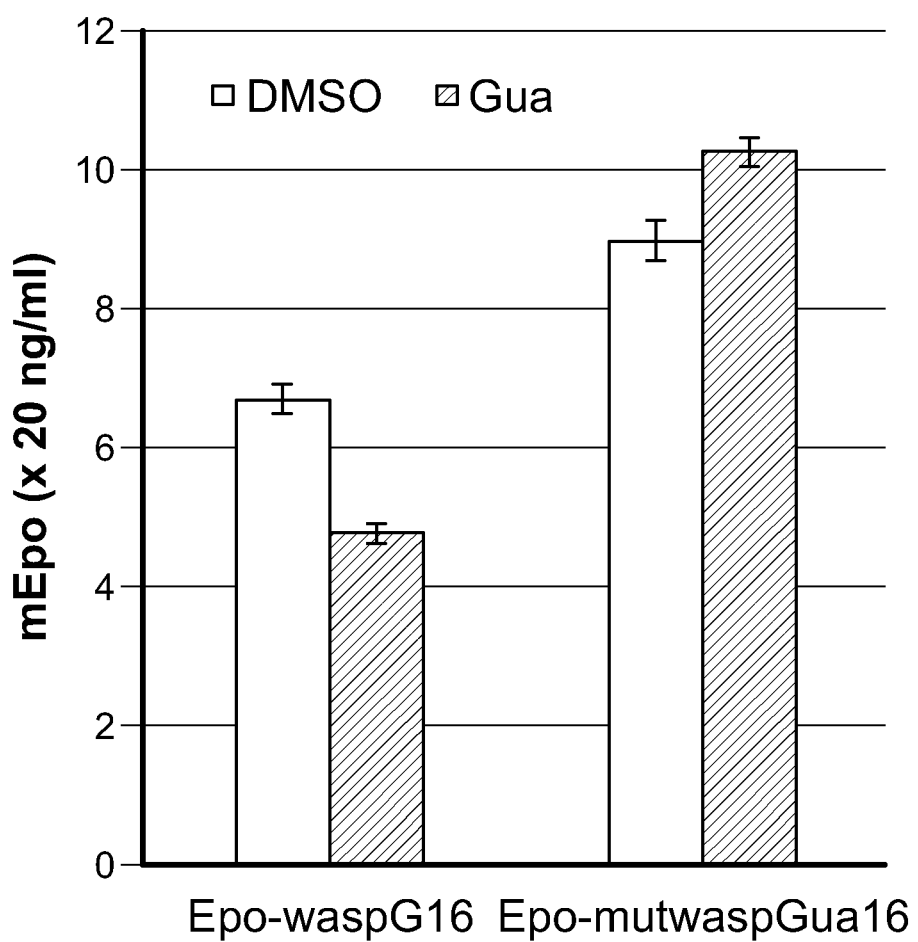

The Luci-waspGua16 construct was then validated in a separate experiment, in which a control construct containing the cleavage-incapable mutant was included. As shown in FIG. 3c, upon guanine treatment, Luci-waspGua16 generated 92% (12-fold) reduction in luciferase activity when compared to the luciferase activity when no guanine was added. In contrast, neither construct pLuc nor Luci-mut-waspGua16 showed any reduction in luciferase activity upon guanine treatment. These results indicate that upon aptamer ligand treatment, the twister ribozyme activity was restored, leading to the reduced production of target gene expression. When guanosine was used at 1 mM as the aptamer ligand, construct Luci-waspG16 yielded 25-fold reduction in luciferase expression (FIG. 3d).

When the waspGua16 was inserted into the 3' UTR of a mouse erythropoietin (Epo) gene, upon guanine treatment, the production of Epo was reduced approximately 30% compared to Epo produced from the solvent-treated control cells. Our results demonstrate that we have generated guanine/guanosine responsive twister ribozyme, a synthetic twister riboswitch which suppresses target gene expression in response to aptamer ligand treatment.

Example 4

Use of Theophylline Aptamer to Regulate Target Gene Expression Via Modulating Twister Ribozyme
Experimental Procedure:

Oligos containing the twister ribozyme sequence linked with theophylline aptamer were synthesized (IDT), and cloned into pLuc vector using Gibson cloning strategy and kit (NEB). Construct sequences were verified by DNA sequencing (Genewiz).

Transfection and firefly luciferase assay: HEK 293 cells were transfected as described in Example 1. Four hours after transfection, the media was aspirated, and new media with or without 2 mM theophylline (Sigma) was added. Luciferase assay was performed 20 to 24 hours after theophylline treatment as described in Example 2. The reduction fold was expressed as the quotient of luciferase activity obtained in the absence of aptamer ligand divided by the value obtained in the presence of the aptamer ligand.

Figure 4A:
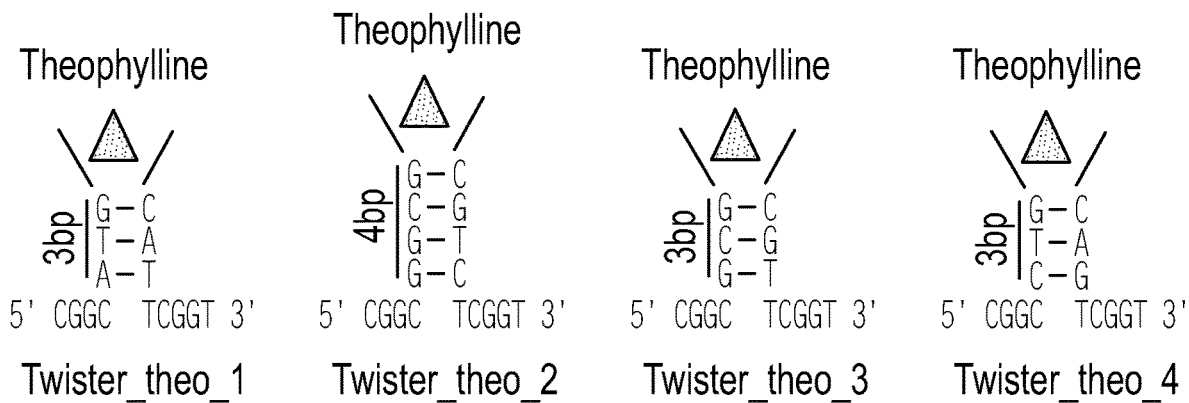
FIGS. 4a-4b. Generation of theophylline responsive twister riboswitches.
Figure 4B:
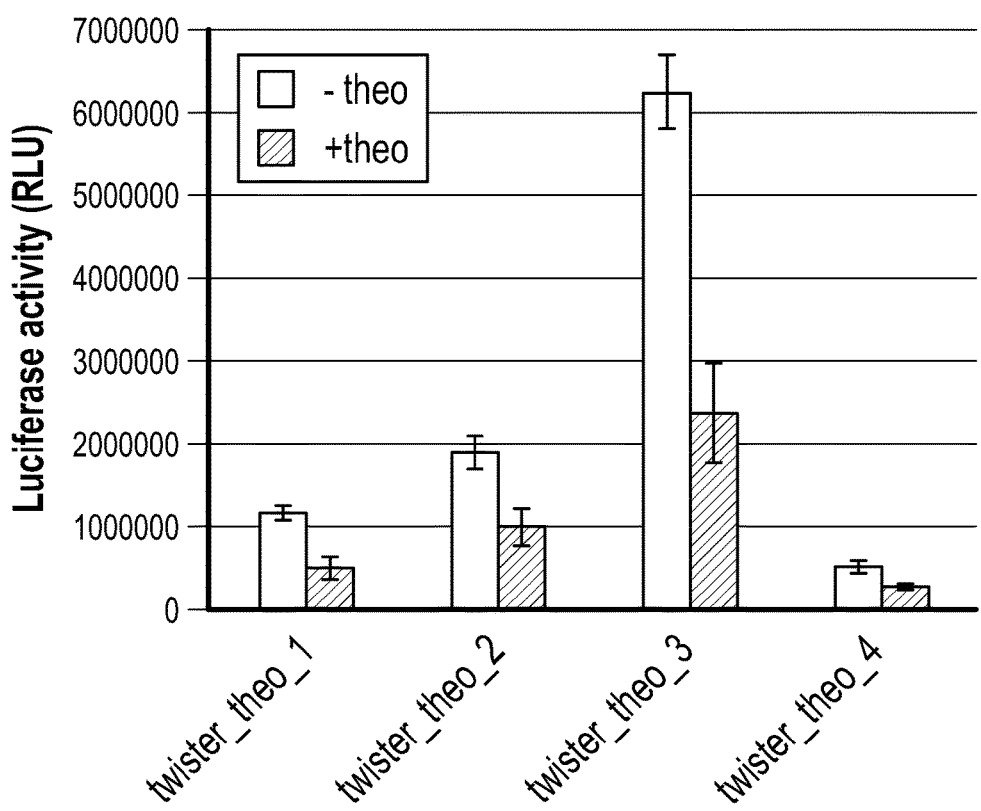

Results:

We tested the use of an additional aptamer in modulating cleavage by twister ribozyme, thereby regulating target gene expression. Based on the 20 Luci-waspGua constructs (1-20) as described in Example 3, either 3 or 4 bp additional stem sequence was used in connecting the theophylline aptamer to loop 2 of twister ribozyme. In addition, the sequence of the stems was varied as shown in FIG. 4a. As shown in FIG. 4b, theophylline treatment resulted in reduction in the luciferase activity in all the constructs when compared to samples without theophylline treatment. Construct twister_theo_3 had a 62% reduction in gene expression upon theophylline treatment. These data demonstrate that we have generated a theophylline responsive twister ribozyme—a synthetic twister riboswitch.

Grafting theophylline aptamer and stem sequences to loop 2 sequence in twister caused different effect on the disruption of twister ribozyme activity, as demonstrated in FIG. 4b in the absence of theophylline treatment. Construct twister_theo_3 showed the most profound disruption of ribozyme activity, and therefore the most robust luciferase activity, in the absence of aptamer ligand. The difference between twister_theo_2 and twister_theo_3 is the length of the stem connecting aptamer and twister, which lead to a difference in disrupting the ribozyme activity. When comparing construct twister_theo_1, 3 and 4 that all have same length of stem (3 bp), the difference resides in the composition of the stem. These results indicate that the sequence composition of the stem also has impact on the ribozyme activity. Therefore, aptamer ligand-responsive ribozyme can be achieved through optimizing the length and the sequence composition of the effector stem region that connects aptamer and twister ribozyme.

Example 5

Self-cleaving ribozymes suppress target gene expression when placed downstream of the translation start codon.
Experimental Procedures:

Plasmid constructs: Synthetic dsDNA (IDT) and standard restriction cloning techniques were used to introduce test sequences into the previously created vector pHDM.2b-LacZ (layout: CMV promoter-intron-LacZ-polyA). All constructs were verified by DNA sequencing.

Transfection: HEK293 cells (ATCC CRL-1573; grown in DMEM, 10% FBS, 37° C., 10% $CO_2$) were plated in 96-well flat bottom plates (100 µL) the day before transfection, such that confluence was about 70% at the time of transfection.

Plasmid DNA (500 ng) was added to a tube or a 96-well U-bottom plate. Separately, TransIT-293 reagent (Mirus; 1.4 µL) was added to 50 µL Optimem I media (Life Technologies), and allowed to sit for 5 minutes at RT. Then, 50 µL of this diluted transfection reagent was added to the DNA, mixed, and incubated at RT for 20 min. Finally, 7 µL of this solution was added to a well of cells in a 96-well plate.

Beta-galactosidase (LacZ) assay: 24 hours after transfection, plates were removed from the incubator, and equilibrated to RT for several minutes on a lab bench, then aspirated. Glo-lysis buffer (Promega, 100 µL, RT) was added, and the plates allowed to remain at room temp at least 5 minutes. Then, the well contents were mixed by 50 µL trituration. A sample of 2 µL was taken from each well and diluted into 200 µL of glo-lysis buffer (101-fold dilution). The dilutions were mixed by trituration, and then 20 µL of each dilution was mixed with 20 µL of beta-glo reagent (Promega) in a solid-white 384-well plate. Thirty minutes later, luminescence was measured for relative light unit (RLU). At most, 96 wells of the 384 were used, in a pattern such that every assayed well was surrounded by either empty wells or the edge of the plate, to reduce cross-talk. All of the measurements fall in the linear range of the assay (determined by comparing various undiluted and diluted samples; data not shown).

Figure 7A:
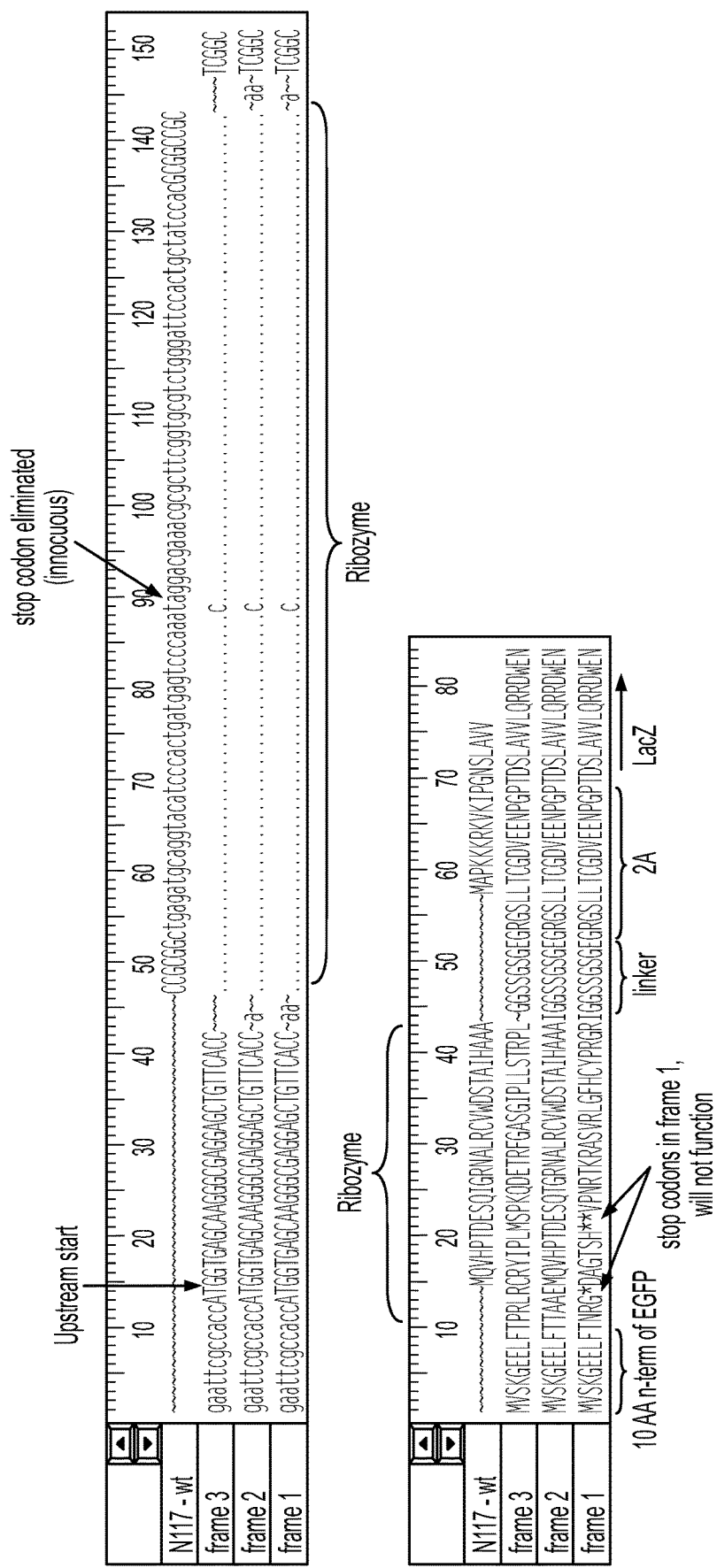
FIG. 7a-7b. Hammerhead ribozyme sequence (7a; SEQ ID NO: 41) and Hairpin ribozyme sequence (7b; SEQ ID NO: 49) placed downstream of translation start codon (SEQ ID NOs: 42-44 and 50-52, respectively). The top panel shows the nucleotide sequence, and the bottom panel shows the translated peptide sequences using different reading frames (SEQ ID NOs: 45-48 and 53-57). The top line in each case is the parent ribozyme, not translated-through; dots in the nucleotide sequence are used to indicate "same as the top line." The 2A peptide sequence from Thoseaasigna virus (T2A) was indicated as 2A. Mutations were made to eliminate potential stop codons in the ribozyme sequences. Translation of reading frame 1 in FIG. 7a contains stop codons as follows: MVSKGEELFTNRG (SEQ ID NO: 48)*DAGTSH (SEQ ID NO: 56)**VPNRTKRASVRLGFHCYPR-GRIGGSSGSGEGRGSLLTCGDVEENPGPTDS LAVVLQRRDWEN (SEQ ID NO: 57), where * represents the position of the stop codons.
Figure 7B:
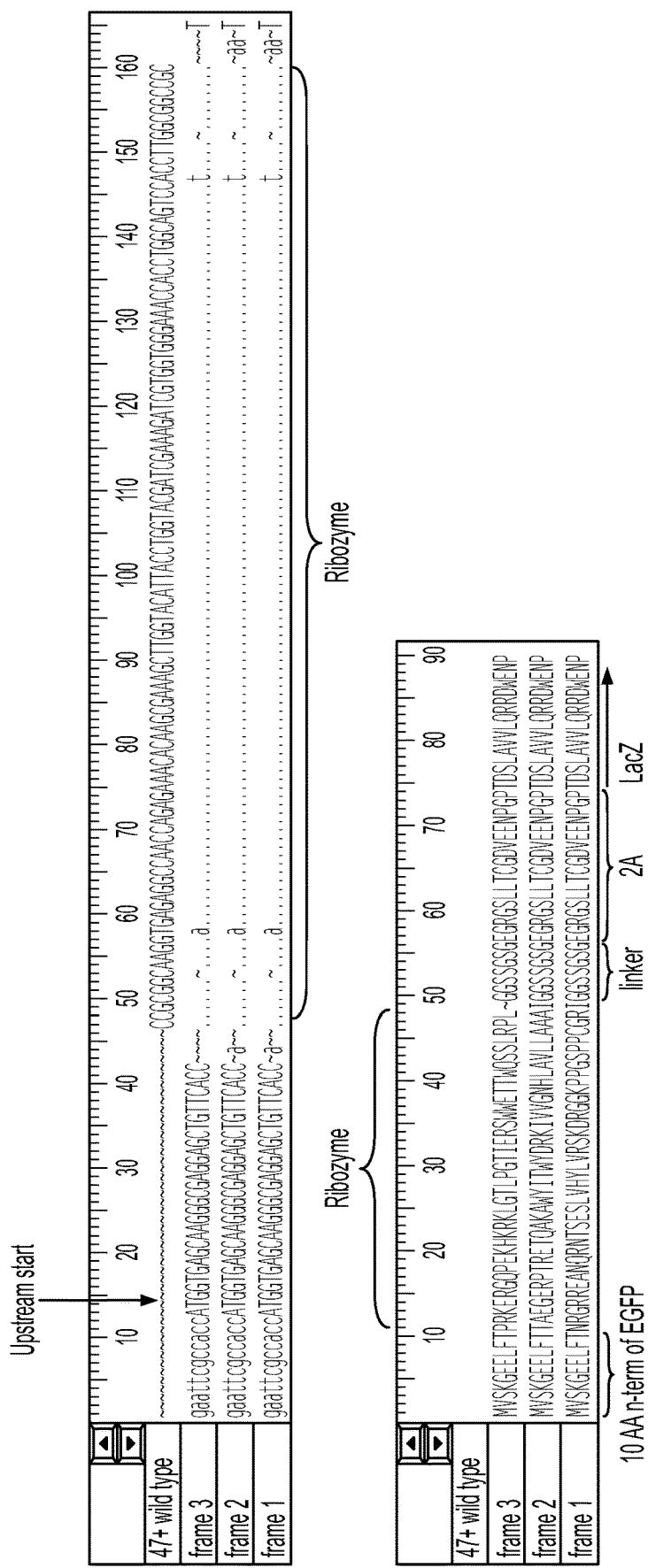

Results: Constructs were made in which the only usable in-frame ATG for a LacZ reporter was upstream of either a hammerhead or hairpin ribozyme (disclosed in U.S. 2015/0056174, see e.g., FIG. 1E, incorporated herein by reference) and for each we made three variants by putting the ribozyme sequence in each possible frame. In all constructs, the ribozyme was followed by linker-2A-peptide-LacZ. Versions with mutant (inactive) ribozymes were also made as controls. Mutations were introduced into each ribozyme to remove potential stop codons. The nucleotide and protein sequences are provided in FIGS. 7a and 7b. (the top line in each case is the parent ribozyme, not translated through; dots in the nucleotide sequence are used to indicate "same as the top line.")

Figure 7C:
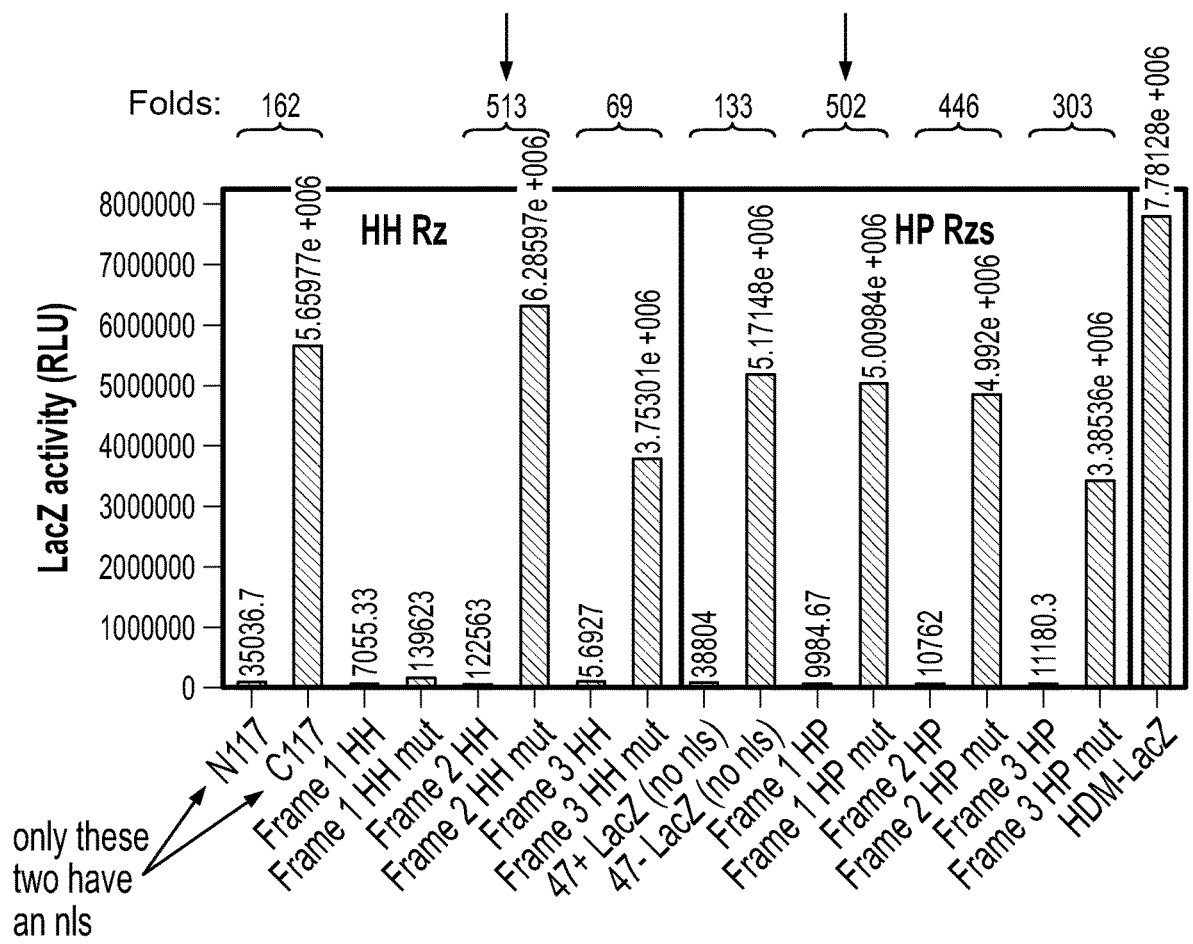
FIG. 7c. Results of Beta-galactosidase activity generated from HEK 293 cells transfected with the indicated constructs. The left half of the graph shows the results from constructs with hammerhead ribozyme sequence, and the right half indicates the results from constructs with Hairpin ribozyme sequence. The fold reduction of the LacZ activity was expressed as the ratio of the value generated from ribozyme inactive mutant construct to the value generated from the ribozyme active construct. The highest fold was indicated by arrow for each ribozyme.

These constructs and their inactivated ribozyme versions were transfected into HEK293 cells, and after 24 hours measured LacZ expression, as shown in FIG. 7c. The results from the hammerhead (HH) ribozymes are shown on the left in FIG. 7c. Placing the HH ribozyme in the 5' UTR gave 162-fold reduction in expression compared to the inactive mutant ribozyme. However, translation-through (frame 2, arrow) gave a much improved 513-fold reduction in expression. Frame 1 does not function, which was expected due to in frame stop codons in the ribozyme sequence that could not be removed. The hairpin (HP) ribozymes are shown on the right in FIG. 7c. Placing the HP ribozyme in the 5' UTR gave 133-fold, but translation in frame 1 resulted in a 502-fold (arrow) reduction in expression. Other frames worked as well. We have made novel ribozyme constructs that show superior gene-control ability compared to published work. Gene expression constructs are described herein where the ribozyme is located not in the UTR, but rather located after the start codon. Control of target gene expression can be significantly enhanced by placing the ribozyme 3' of the translation start as compared to ribozyme placement in the 5' UTR. When the ribozyme is placed downstream of the translation start, self-cleavage removes the start codon from the rest of the mRNA of the target gene, resulting in decreased residual background expression.

Example 6

Guanine-responsive twister riboswitch functions downstream translation start codon.

Experimental Procedures:

Oligos containing either a start codon or coding sequence for the first 10 amino acids of GFP and waspGua16 followed by a linker2A sequence were synthesized (IDT) and cloned into the pLuc vector using the Gibson cloning strategy and cloning kit (NEB). Transfection and luciferase assay of cultured cells were performed as described in Example 3.

Figure 5A:
FIGS. 5a-5b. The portability of twister riboswitch in mammalian cells.
Figure 5A:
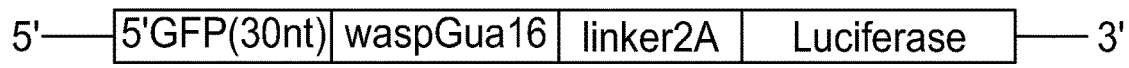
Figure 5B:
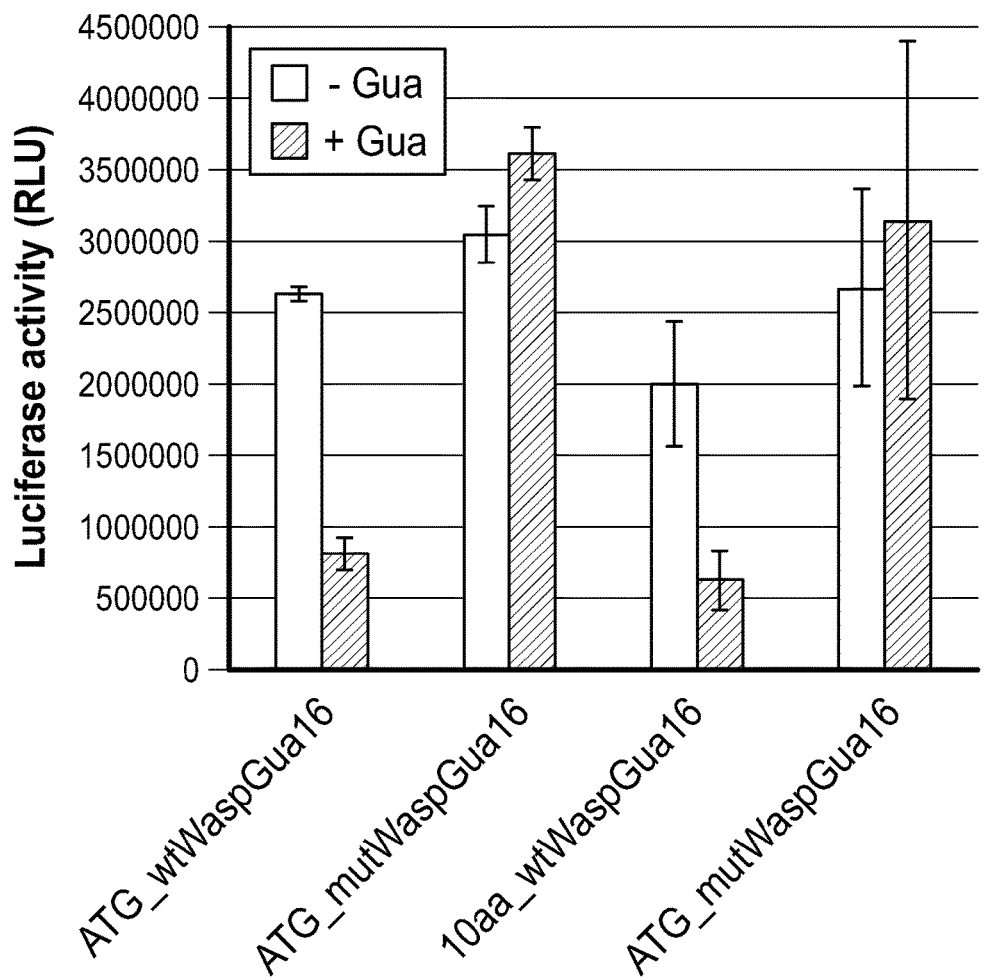

Results:

To test the portability of aptamer ligand-responsive twister ribozyme, we placed the waspGua16 sequence downstream of either (i) the translation start codon of the luciferase gene or (ii) the coding sequence for the first 10 aa of GFP, as illustrated in FIG. 5a. Fusing the twister riboswitch sequence with a downstream target gene would create an N-terminal tag when the target gene product is expressed, which may potentially affect the protein function. To remove this N-terminal tag, a linker2A sequence was inserted between twister riboswitch and downstream target gene sequence. As shown in FIG. 5b, insertion of the twister riboswitch polynucleotide cassette did not impair luciferase gene expression in the absence of aptamer ligand, guanine, indicating the disrupted ribozyme activity. However, in the presence of guanine, luciferase gene expression was reduced 68% of the untreated control for both ATG_waspGua16 and 10aa_waspGua16 constructs, while the control constructs that contain the mutant twister sequence showed no reduction in luciferase expression in response to guanine treatment. This result demonstrates that the reduction in target gene expression with the polynucleotide cassette containing the functional twister riboswitches was due to restoration of twister ribozyme activity by aptamer/ligand binding. Our results indicate that twister riboswitch functions downstream start codon in the coding sequence, demonstrating the portability of the polynucleotide cassette containing the synthetic twister riboswitch.

Example 7

Use of Guanine Aptamer to Generate Guanine Responsive ON Twister Riboswitch

Experimental Procedures:

Plasmid constructs: Oligos containing aptamer sequence linker to the P1 stem of twister ribozyme were synthesized (IDT) and cloned into pLuc vector using Gibson cloning strategy and cloning kit (NEB).

Transfection was performed as described in Example 1, and firefly luciferase assay was performed as described in Example 3.

Results:

The twister riboswitches described in Examples 3 and 4 suppress target gene expression in response to the aptamer ligand treatment, and thus are OFF twister riboswitches. Here, a different strategy was employed for linking the aptamer sequence to the twister ribozyme generating ON twister riboswitches that induce target gene expression upon aptamer ligand treatment. As shown in FIG. 6a, the 3' end of the twister P1 stem (including the additional 3 bp stem) is adjacent to the aptamer sequence. In this configuration, stem sequence is shared between the twister P1 stem and the aptamer P1 stem such that the shared sequence can either form the twister P1 stem or the aptamer P1 stem. In the absence of the aptamer ligand (top panel), the aptamer sequence adjacent to the twister P1 stem does not disrupt twister structure and its ribozyme cleavage activity remains intact, leading to cleavage of the mRNA and inhibition of target gene expression. In the presence of aptamer ligand (lower panel), the ligand-bound aptamer forms the aptamer P1 stem with the shared sequence from the twister P1 stem thereby disrupting twister P1 stem formation, and disrupting its ribozyme activity and increasing target gene expression. As described in Examples 3 and 4, the length of the aptamer P1 stem is important in its regulating function in the context of a riboswitch. If the stem length is too long, the aptamer P1 formation becomes aptamer ligand independent, leading to unregulatable target gene expression. In addition, we speculated that the length of the shared sequence would be important as well. If the length of the shared stem sequence is too short, the twister ribozyme may not be affected by aptamer P1 stem formation.

ON twister riboswitches were created having either 6 or 7 nt of the twister P1 stem sequence shared with aptamer P1 stem. With the 6 or 7 nt shared stem sequences, the aptamer forms an 8 or 9 bp P1 stem. An xpt-guanine aptamer was linked to either the 5' or 3' arm of the twister P1 stem sequence, generating GT8 or TG8 and TG9 constructs.

Linking the guanine aptamer to the 5' arm of the twister P1 stem (construct GT8) provided 1.4 fold induction of luciferase activity upon guanosine treatment, as shown in FIG. 6b, left panel. However, when aptamer was linked to the 3' end of the twister P1 stem as illustrated in FIG. 6a, the basal level of luciferase activity was reduced to 0.7% of the control vector that does not contain twister/aptamer sequences in 3' UTR. Upon guanosine treatment, luciferase activity was induced generating 8.6-fold and 9.2-fold induction from construct TG8 and TG9, respectively, as shown in FIG. 6b (middle and right panels). The low basal level expression of luciferase from construct TG8 and TG9 indicates that linking aptamer to the 3' end of P1 stem did not disrupt ribozyme activity, and upon aptamer/ligand binding, the twister ribozyme activity was impaired, thus leading to increased target gene expression. These results demonstrate that we have generated novel twister ON riboswitches that induce target gene expression in response to aptamer ligand treatment.

SEQUENCE LISTING

```
Sequence total quantity: 57
SEQ ID NO: 1            moltype = DNA  length = 208
FEATURE                 Location/Qualifiers
misc_feature            1..208
                        note = wasp-twister in pEGFP-C1
source                  1..208
                        mol_type = other DNA
                        organism = synthetic construct
SEQUENCE: 1
gtgaccgccg ccgggatcac tctcggcatg gacgagctgt acaagtaaac cgcggcttgt   60
aatgcggccg tgtaaataat ttacacgtcg gtctcaagcc cgataaacgc agagagcaag  120
gcggccgcca taccacattt gtagaggttt tacttgcttt aaaaaacctc ccacacctcc  180
ccctgaacct gaaacataaa atgaatgc                                     208

SEQ ID NO: 2            moltype = DNA  length = 217
FEATURE                 Location/Qualifiers
misc_feature            1..217
                        note = es-twister in pEGFPC1
source                  1..217
                        mol_type = other DNA
                        organism = synthetic construct
SEQUENCE: 2
gtgaccgccg ccgggatcac tctcggcatg gacgagctgt acaagtaaac cgcggcaata   60
aagcggttac aagcccgcaa aaatagcaga gtaatgtcgc gatagcgcgg cattaatgca  120
gctttattgg cggccgccat accacatttg tagaggtttt acttgcttta aaaaacctcc  180
cacacctccc cctgaacctg aaacataaaa tgaatgc                           217

SEQ ID NO: 3            moltype = DNA  length = 208
FEATURE                 Location/Qualifiers
misc_feature            1..208
                        note = wasp-twister-mut in pEGFP-C1
source                  1..208
                        mol_type = other DNA
                        organism = synthetic construct
SEQUENCE: 3
gtgaccgccg ccgggatcac tctcggcatg gacgagctgt acaagtaaac cgcggcttgt   60
gatgcggccg tgtaaataat ttacacgtcg gtctcaagcc cgataaacgc agagagcaag  120
gcggccgcca taccacattt gtagaggttt tacttgcttt aaaaaacctc ccacacctcc  180
ccctgaacct gaaacataaa atgaatgc                                     208

SEQ ID NO: 4            moltype = DNA  length = 202
FEATURE                 Location/Qualifiers
misc_feature            1..202
                        note = wasp_no Sac 0HP in pEGFP-C1
source                  1..202
                        mol_type = other DNA
                        organism = synthetic construct
SEQUENCE: 4
gtgaccgccg ccgggatcac tctcggcatg gacgagctgt acaagtaaac ttgtaatgcg   60
gccgtgtaaa taatttacac gtcggtctca agcccgataa acgcagagag caaggcggcc  120
gccataccac atttgtagag gttttacttg ctttaaaaaa cctcccacac ctcccctga   180
acctgaaaca taaatgaat gc                                            202

SEQ ID NO: 5            moltype = DNA  length = 205
```

```
FEATURE                 Location/Qualifiers
misc_feature            1..205
                        note = wasp_no Sac 3HP in pEGFP-C1
source                  1..205
                        mol_type = other DNA
                        organism = synthetic construct
SEQUENCE: 5
gtgaccgccg ccgggatcac tctcggcatg gacgagctgt acaagtaaac gccttgtaat    60
gcggccgtgt aaataattta cacgtcggtc tcaagcccga taaacgcaga gagcaaggcg   120
gccgccatac cacatttgta gaggttttac ttgctttaaa aaacctccca cacctccccc   180
tgaacctgaa acataaaatg aatgc                                         205

SEQ ID NO: 6            moltype = DNA  length = 203
FEATURE                 Location/Qualifiers
misc_feature            1..203
                        note = wasp_No Sac 0HP in pLuc
source                  1..203
                        mol_type = other DNA
                        organism = synthetic construct
SEQUENCE: 6
tcagagagat cctcataaag gccaagaagg gcggaaagat cgccgtgtaa acttgtaatg    60
cggccgtgta aataatttac acgtcggtct caagcccgat aaacgcagag agcaaggcg   120
ccgccatacc acatttgtag aggttttact tgctttaaaa aacctccac acctccccct   180
gaacctgaaa cataaaatga atg                                           203

SEQ ID NO: 7            moltype = DNA  length = 207
FEATURE                 Location/Qualifiers
misc_feature            1..207
                        note = wasp_No Sac 3HP in pLuc
source                  1..207
                        mol_type = other DNA
                        organism = synthetic construct
SEQUENCE: 7
tcagagagat cctcataaag gccaagaagg gcggaaagat cgccgtgtaa acgccttgta    60
atgcggccgt gtaaataatt tacacgtcgg tctcaagccc gataaacgca gagagcaagg   120
cggccgccat accacatttg tagaggtttt acttgcttta aaaaacctcc cacacctccc   180
cctgaacctg aaacataaaa tgaatgc                                       207

SEQ ID NO: 8            moltype = DNA  length = 275
FEATURE                 Location/Qualifiers
misc_feature            1..275
                        note = waspGua1 in pLuc
source                  1..275
                        mol_type = other DNA
                        organism = synthetic construct
SEQUENCE: 8
tcagagagat cctcataaag gccaagaagg gcggaaagat cgccgtgtaa acgccttgta    60
atgcggccgt gtaaatcact catataatcg cgtggatatg gcacgcaagt ttctaccggg   120
caccgtaaat gtccgactat gggtgattta cacgtcggtc tcaagcccga taaacgcaga   180
gagcaaggcg gccgccatac cacatttgta gaggttttac ttgctttaaa aaacctccca   240
cacctccccc tgaacctgaa acataaaatg aatgc                              275

SEQ ID NO: 9            moltype = DNA  length = 271
FEATURE                 Location/Qualifiers
misc_feature            1..271
                        note = waspGua2 in pLuc
source                  1..271
                        mol_type = other DNA
                        organism = synthetic construct
SEQUENCE: 9
tcagagagat cctcataaag gccaagaagg gcggaaagat cgccgtgtaa acgccttgta    60
atgcggccgt gtaaaactca tataatcgcg tggatatggc acgcaagttt ctaccggca   120
ccgtaaatgt ccgactatgg gttttacacg tcggtctcaa gcccgataaa cgcagagagc   180
aaggcggccg ccataccaca tttgtagagg ttttacttgc tttaaaaaac ctcccacacc   240
tcccctgaa cctgaaacat aaaatgaatg c                                   271

SEQ ID NO: 10           moltype = DNA  length = 267
FEATURE                 Location/Qualifiers
misc_feature            1..267
                        note = waspGua3 in pLuc
source                  1..267
                        mol_type = other DNA
                        organism = synthetic construct
SEQUENCE: 10
tcagagagat cctcataaag gccaagaagg gcggaaagat cgccgtgtaa acgccttgta    60
atgcggccgt gtaactcata taatcgcgtg gatatggcac gcaagtttct accgggcacc   120
gtaaatgtcc gactatgggt tacacgtcgg tctcaagccc gataaacgca gagagcaagg   180
cggccgccat accacatttg tagaggtttt acttgcttta aaaaacctcc cacacctccc   240
cctgaacctg aaacataaaa tgaatgc                                       267
```

```
SEQ ID NO: 11            moltype = DNA   length = 263
FEATURE                  Location/Qualifiers
misc_feature             1..263
                         note = waspGua4 in pLuc
source                   1..263
                         mol_type = other DNA
                         organism = synthetic construct
SEQUENCE: 11
tcagagagat cctcataaag gccaagaagg gcggaaagat cgccgtgtaa acgccttgta    60
atgcggccgt gtatcatata atcgcgtgga tatggcacgc aagtttctac cgggcaccgt   120
aaatgtccga ctatggtaca cgtcggtctc aagcccgata acgcagaga gcaaggcggc   180
cgccatacca catttgtaga ggttttactt gctttaaaaa acctcccaca cctcccctg   240
aacctgaaac ataaaatgaa tgc                                           263

SEQ ID NO: 12            moltype = DNA   length = 261
FEATURE                  Location/Qualifiers
misc_feature             1..261
                         note = waspGua5 in pLuc
source                   1..261
                         mol_type = other DNA
                         organism = synthetic construct
SEQUENCE: 12
tcagagagat cctcataaag gccaagaagg gcggaaagat cgccgtgtaa acgccttgta    60
atgcggccgt gttcatataa tcgcgtggat atggcacgca agtttctacc gggcaccgta   120
aatgtccgac tatggacacg tcggtctcaa gcccgataaa cgcagagagc aaggcggccg   180
ccataccaca tttgtagagg ttttacttgc tttaaaaaac ctcccacacc tcccctgaa   240
cctgaaacat aaaatgaatg c                                             261

SEQ ID NO: 13            moltype = DNA   length = 259
FEATURE                  Location/Qualifiers
misc_feature             1..259
                         note = waspGua6 in pLuc
source                   1..259
                         mol_type = other DNA
                         organism = synthetic construct
SEQUENCE: 13
tcagagagat cctcataaag gccaagaagg gcggaaagat cgccgtgtaa acgccttgta    60
atgcggccgt gtcatataat cgcgtggata tggcacgcaa gtttctaccg ggcaccgtaa   120
atgtccgact atgacacgtc ggtctcaagc ccgataaacg cagagagcaa ggcggccgcc   180
ataccacatt tgtagaggtt ttacttgctt taaaaaacct cccacacctc ccctgaacc   240
tgaaacataa aatgaatgc                                                259

SEQ ID NO: 14            moltype = DNA   length = 257
FEATURE                  Location/Qualifiers
misc_feature             1..257
                         note = waspGua7 in pLuc
source                   1..257
                         mol_type = other DNA
                         organism = synthetic construct
SEQUENCE: 14
tcagagagat cctcataaag gccaagaagg gcggaaagat cgccgtgtaa acgccttgta    60
atgcggccgt gcatataatc gcgtggatat ggcacgcaag tttctaccgg caccgtaaa   120
tgtccgacta tgcacgtcgg tctcaagccc gataaacgca gagagcaagg cggccgccat   180
accacatttg tagaggtttt acttgcttta aaaaacctcc cacacctccc cctgaacctg   240
aaacataaaa tgaatgc                                                  257

SEQ ID NO: 15            moltype = DNA   length = 255
FEATURE                  Location/Qualifiers
misc_feature             1..255
                         note = waspGua8 in pLuc
source                   1..255
                         mol_type = other DNA
                         organism = synthetic construct
SEQUENCE: 15
tcagagagat cctcataaag gccaagaagg gcggaaagat cgccgtgtaa acgccttgta    60
atgcggccgt gatataatcg cgtggatatg gcacgcaagt ttctaccggg caccgtaaat   120
gtccgactat acgtcggtc tcaagcccga taaacgcaga gagcaaggcg gccgccatac   180
cacatttgta gaggttttac ttgctttaaa aaacctccca cacctccccc tgaacctgaa   240
acataaaatg aatgc                                                    255

SEQ ID NO: 16            moltype = DNA   length = 253
FEATURE                  Location/Qualifiers
misc_feature             1..253
                         note = waspGua9 in pLuc
source                   1..253
                         mol_type = other DNA
                         organism = synthetic construct
SEQUENCE: 16
```

```
tcagagagat cctcataaag gccaagaagg gcggaaagat cgccgtgtaa acgccttgta   60
atgcggccgt atataatcgc gtggatatgc cacgcaagtt tctaccgggc accgtaaatg  120
tccgactata cgtcggtctc aagcccgata acgcagaga  gcaaggcggc cgccatacca  180
catttgtaga ggttttactt gctttaaaaa acctcccaca cctcccctg  aacctgaaac  240
ataaaatgaa tgc                                                     253

SEQ ID NO: 17          moltype = DNA  length = 247
FEATURE                Location/Qualifiers
misc_feature           1..247
                       note = waspGua12 in pLuc
source                 1..247
                       mol_type = other DNA
                       organism = synthetic construct
SEQUENCE: 17
tcagagagat cctcataaag gccaagaagg gcggaaagat cgccgtgtaa acgccttgta   60
atgcggccga taatcgcgtg gatatggcac gcaagtttct accgggcacc gtaaatgtcc  120
gactcgtcgg tctcaagccc gataaacgca gagagcaagg cggccgccat accacatttg  180
tagaggtttt acttgcttta aaaaacctcc cacacctccc cctgaacctg aaacataaaa  240
tgaatgc                                                            247

SEQ ID NO: 18          moltype = DNA  length = 245
FEATURE                Location/Qualifiers
misc_feature           1..245
                       note = waspGua13 in pLuc
source                 1..245
                       mol_type = other DNA
                       organism = synthetic construct
SEQUENCE: 18
tcagagagat cctcataaag gccaagaagg gcggaaagat cgccgtgtaa acgccttgta   60
atgcggccat aatcgcgtgg atatggcacg caagtttcta ccgggcaccg taaatgtccg  120
actgtcggtc tcaagcccga taaacgcaga gagcaaggcg gccgccatac cacatttgtg  180
gaggttttac ttgctttaaa aaacctccca cacctccccc tgaacctgaa acataaaatg  240
aatgc                                                              245

SEQ ID NO: 19          moltype = DNA  length = 243
FEATURE                Location/Qualifiers
misc_feature           1..243
                       note = waspGua14 in pLuc
source                 1..243
                       mol_type = other DNA
                       organism = synthetic construct
SEQUENCE: 19
tcagagagat cctcataaag gccaagaagg gcggaaagat cgccgtgtaa acgccttgta   60
atgcggccta atcgcgtgga tatggcacgc aagtttctac cgggcaccgt aaatgtccga  120
cgtcggtctc aagcccgata acgcagaga  gcaaggcggc cgccatacca catttgtaga  180
ggttttactt gctttaaaaa acctcccaca cctcccctg  aacctgaaac ataaaatgaa  240
tgc                                                                243

SEQ ID NO: 20          moltype = DNA  length = 249
FEATURE                Location/Qualifiers
misc_feature           1..249
                       note = waspGua15 in pLuc
source                 1..249
                       mol_type = other DNA
                       organism = synthetic construct
SEQUENCE: 20
tcagagagat cctcataaag gccaagaagg gcggaaagat cgccgtgtaa acgccttgta   60
atgcggccat ataatcgcgt ggatatggca cgcaagtttc taccgggcac cgtaaatgtc  120
cgactatgtc ggtctcaagc ccgataaacg cagagagcaa ggcggccgcc ataccacatt  180
tgtagaggtt ttacttgctt taaaaaacct cccacacctc ccctgaaacc tgaaacataa  240
aatgaatgc                                                          249

SEQ ID NO: 21          moltype = DNA  length = 247
FEATURE                Location/Qualifiers
misc_feature           1..247
                       note = waspGua16 in pLuc
source                 1..247
                       mol_type = other DNA
                       organism = synthetic construct
SEQUENCE: 21
tcagagagat cctcataaag gccaagaagg gcggaaagat cgccgtgtaa acgccttgta   60
atgcggcata taatcgcgtg gatatggcac gcaagtttct accgggcacc gtaaatgtcc  120
gactattcgg tctcaagccc gataaacgca gagagcaagg cggccgccat accacatttg  180
tagaggtttt acttgcttta aaaaacctcc cacacctccc cctgaacctg aaacataaaa  240
tgaatgc                                                            247

SEQ ID NO: 22          moltype = DNA  length = 245
FEATURE                Location/Qualifiers
misc_feature           1..245
```

```
                    note = waspGua17 in pLuc
source              1..245
                    mol_type = other DNA
                    organism = synthetic construct
SEQUENCE: 22
tcagagagat cctcataaag gccaagaagg gcggaaagat cgccgtgtaa acgccttgta    60
atgcggctat aatcgcgtgg atatggcacg caagtttcta ccgggcaccg taaatgtccg   120
actatcggtc tcaagcccga taaacgcaga gagcaaggcg gccgccatac cacatttgta   180
gaggttttac ttgcttttaaa aaacctccca cacctccccc tgaacctgaa acataaaatg   240
aatgc                                                               245

SEQ ID NO: 23            moltype = DNA  length = 253
FEATURE                  Location/Qualifiers
misc_feature             1..253
                    note = waspGua18 in pLuc
source              1..253
                    mol_type = other DNA
                    organism = synthetic construct
SEQUENCE: 23
tcagagagat cctcataaag gccaagaagg gcggaaagat cgccgtgtaa acgccttgta    60
atgcggccgt gtataatcgc gtggatatgg cacgcaagtt tctaccgggc accgtaaatg   120
tccgactaca cgtcggtctc aagcccgata aacgcagaga gcaaggcggc cgccatacca   180
catttgtaga ggttttactt gctttaaaaa acctcccaca cctcccctg aacctgaaac     240
ataaaatgaa tgc                                                      253

SEQ ID NO: 24            moltype = DNA  length = 251
FEATURE                  Location/Qualifiers
misc_feature             1..251
                    note = waspGua19 in pLuc
source              1..251
                    mol_type = other DNA
                    organism = synthetic construct
SEQUENCE: 24
tcagagagat cctcataaag gccaagaagg gcggaaagat cgccgtgtaa acgccttgta    60
atgcggccgt tataatcgcg tggatatggc acgcaagttt ctaccgggca ccgtaaatgt   120
ccgactaacg tcggtctcaa gcccgataaa cgcagagagc aaggcggccg ccataccaca   180
tttgtagagg ttttacttgc tttaaaaaac ctcccacacc tcccctgaa cctgaaacat     240
aaaatgaatg c                                                        251

SEQ ID NO: 25            moltype = DNA  length = 249
FEATURE                  Location/Qualifiers
misc_feature             1..249
                    note = waspGua20 in pLuc
source              1..249
                    mol_type = other DNA
                    organism = synthetic construct
SEQUENCE: 25
tcagagagat cctcataaag gccaagaagg gcggaaagat cgccgtgtaa acgccttgta    60
atgcggccgt ataatcgcgt ggatatggca cgcaagtttc taccgggcac cgtaaatgtc   120
cgactacgtc ggtctcaagc ccgataaacg cagagagcaa ggcggccgcc ataccacatt   180
tgtagaggtt ttacttgctt taaaaaacct cccacacctc ccctgaacc tgaaacataa     240
aatgaatgc                                                           249

SEQ ID NO: 26            moltype = DNA  length = 296
FEATURE                  Location/Qualifiers
misc_feature             1..296
                    note = Epo-waspGua16
source              1..296
                    mol_type = other DNA
                    organism = synthetic construct
SEQUENCE: 26
gctgtacacg ggagaggtct gcaggagagg ggacaggtga ggatccacgc cttgtaatgc    60
ggcatataat cgcgtggata tggcacgcaa gtttctaccg gcaccgtaa atgtccgact    120
attcggtctc aagcccgata aacgcagaga gcaaggccca gatctaattc               180
acccccaccag tgcaggctgc ctatcagaaa gtggtggctg gtgtggctaa tgccctggcc   240
cacaagtatc actaagctcg ctttcttgct gtccaatttc tattaaaggt tccttt        296

SEQ ID NO: 27            moltype = DNA  length = 296
FEATURE                  Location/Qualifiers
misc_feature             1..296
                    note = Epo-mutwaspGua16
source              1..296
                    mol_type = other DNA
                    organism = synthetic construct
SEQUENCE: 27
gctgtacacg ggagaggtct gcaggagagg ggacaggtga ggatccacgc cttgtgatgc    60
ggcatataat cgcgtggata tggcacgcaa gtttctaccg gcaccgtaa atgtccgact    120
attcggtctc aagcccgata aacgcagaga gcaaggcgct cgagggccca gatctaattc   180
acccccaccag tgcaggctgc ctatcagaaa gtggtggctg gtgtggctaa tgccctggcc   240
```

```
cacaagtatc actaagctcg ctttcttgct gtccaatttc tattaaaggt tcctttt          296

SEQ ID NO: 28              moltype = DNA   length = 219
FEATURE                    Location/Qualifiers
misc_feature               1..219
                           note = twister_theo_1 in pLuc
source                     1..219
                           mol_type = other DNA
                           organism = synthetic construct
SEQUENCE: 28
tcagagagat cctcataaag gccaagaagg gcggaaagat cgccgtgtaa acgccttgta          60
atgcggcatg ataccagccg aaaggccctt ggcagcattc ggtctcaagc ccgataaacg         120
cagagagcaa ggcggccgcc ataccacatt tgtagaggtt ttacttgctt taaaaaacct        180
cccacacctc ccccctgaacc tgaaacataa aatgaatgc                              219

SEQ ID NO: 29              moltype = DNA   length = 221
FEATURE                    Location/Qualifiers
misc_feature               1..221
                           note = twister_theo_2 in pLuc
source                     1..221
                           mol_type = other DNA
                           organism = synthetic construct
SEQUENCE: 29
tcagagagat cctcataaag gccaagaagg gcggaaagat cgccgtgtaa acgccttgta          60
atgcggcggc gataccagcc gaaaggccct tggcagcgtc tcggtctcaa gcccgataaa         120
cgcagagagc aaggcggccg ccataccaca tttgtagagg ttttacttgc tttaaaaaac         180
ctcccacacc tccccctgaa cctgaaacat aaaatgaatg c                            221

SEQ ID NO: 30              moltype = DNA   length = 219
FEATURE                    Location/Qualifiers
misc_feature               1..219
                           note = twister_theo_3 in pLuc
source                     1..219
                           mol_type = other DNA
                           organism = synthetic construct
SEQUENCE: 30
tcagagagat cctcataaag gccaagaagg gcggaaagat cgccgtgtaa acgccttgta          60
atgcggcgcg ataccagccg aaaggccctt ggcagcgttc ggtctcaagc ccgataaacg        120
cagagagcaa ggcggccgcc ataccacatt tgtagaggtt ttacttgctt taaaaaacct        180
cccacacctc ccccctgaacc tgaaacataa aatgaatgc                              219

SEQ ID NO: 31              moltype = DNA   length = 219
FEATURE                    Location/Qualifiers
misc_feature               1..219
                           note = twister_theo_4 in pLuc
source                     1..219
                           mol_type = other DNA
                           organism = synthetic construct
SEQUENCE: 31
tcagagagat cctcataaag gccaagaagg gcggaaagat cgccgtgtaa acgccttgta          60
atgcggcctg ataccagccg aaaggccctt ggcagcgtc ggtctcaagc ccgataaacg         120
cagagagcaa ggcggccgcc ataccacatt tgtagaggtt ttacttgctt taaaaaacct        180
cccacacctc ccccctgaacc tgaaacataa aatgaatgc                              219

SEQ ID NO: 32              moltype = DNA   length = 228
FEATURE                    Location/Qualifiers
misc_feature               1..228
                           note = ATG_wtWaspGua16 in pLuc
source                     1..228
                           mol_type = other DNA
                           organism = synthetic construct
SEQUENCE: 32
atgacgcctt gtaatgcggc atataatcgc gtggatatgg cacgcaagtt tctaccgggc          60
accgtaaatg tccgactatt cggtctcaag cccgataaac gcagagagca aggcgaaggc         120
ggatcttcag gtagtggcga gggcagagga agtcttctaa catgcggtga cgtggaggag        180
aatcccggcc ccgaagacgc caaaaacata aagaaaggcc ggcgcca                      228

SEQ ID NO: 33              moltype = DNA   length = 228
FEATURE                    Location/Qualifiers
misc_feature               1..228
                           note = ATG_mutWaspGua16 in pLuc
source                     1..228
                           mol_type = other DNA
                           organism = synthetic construct
SEQUENCE: 33
atgacgcctt gtgatgcggc atataatcgc gtggatatgg cacgcaagtt tctaccgggc          60
accgtaaatg tccgactatt cggtctcaag cccgataaac gcagagagca aggcgaaggc         120
ggatcttcag gtagtggcga gggcagagga agtcttctaa catgcggtga cgtggaggag        180
aatcccggcc ccgaagacgc caaaaacata aagaaaggcc ggcgcca                      228
```

```
SEQ ID NO: 34          moltype = DNA  length = 255
FEATURE                Location/Qualifiers
misc_feature           1..255
                       note = 10aa_wtWaspGua16 in pLuc
source                 1..255
                       mol_type = other DNA
                       organism = synthetic construct
SEQUENCE: 34
atggtgagca agggcgagga gctgttcacc acgccttgta atgcggcata taatcgcgtg    60
gatatggcac gcaagtttct accgggcacc gtaaatgtcc gactattcgg tctcaagccc   120
gataaacgca gagagcaagg cgaaggcgga tcttcaggta gtggcgaggg cagaggaagt   180
cttctaacat gcggtgacgt ggaggagaat cccggccccg aagacgccaa aaacataaag   240
aaaggcccgg cgcca                                                    255

SEQ ID NO: 35          moltype = DNA  length = 255
FEATURE                Location/Qualifiers
misc_feature           1..255
                       note = 10aa_mutWaspGua16 in pLuc
source                 1..255
                       mol_type = other DNA
                       organism = synthetic construct
SEQUENCE: 35
atggtgagca agggcgagga gctgttcacc acgccttgtg atgcggcata taatcgcgtg    60
gatatggcac gcaagtttct accgggcacc gtaaatgtcc gactattcgg tctcaagccc   120
gataaacgca gagagcaagg cgaaggcgga tcttcaggta gtggcgaggg cagaggaagt   180
cttctaacat gcggtgacgt ggaggagaat cccggccccg aagacgccaa aaacataaag   240
aaaggcccgg cgcca                                                    255

SEQ ID NO: 36          moltype = DNA  length = 271
FEATURE                Location/Qualifiers
misc_feature           1..271
                       note = GT_8bp in pLuc
source                 1..271
                       mol_type = other DNA
                       organism = synthetic construct
SEQUENCE: 36
tcagagagat cctcataaag gccaagaagg gcggaaagat cgccgtgtaa taaaggcgta    60
taatcgcgtg gatatggcac gcaagtttct accgggcacc gtaaatgtcc gactacgcct   120
tgtaatgcgg ccgtgtaaat aatttacacg tcggtctcaa gcccgataaa cgcagagagc   180
aaggcggccg ccataccaca tttgtagagg ttttacttgc tttaaaaaac ctcccacacc   240
tccccctgaa cctgaaacat aaaatgaatg c                                  271

SEQ ID NO: 37          moltype = DNA  length = 265
FEATURE                Location/Qualifiers
misc_feature           1..265
                       note = TG_9b in pLuc
source                 1..265
                       mol_type = other DNA
                       organism = synthetic construct
SEQUENCE: 37
tcagagagat cctcataaag gccaagaagg gcggaaagat cgccgtgtaa acgccttgta    60
atgcggccgt gtaaataatt tacacgtcgg tctcaagccc gataaacgca gagagcaagg   120
cgtataatcg cgtggatatg gcacgcaagt ttctaccggg caccgtaaat gtccgactac   180
gccttgatac cacatttgta gaggttttac ttgctttaaa aaacctccca cacctccccc   240
tgaacctgaa acataaaatg aatgc                                         265

SEQ ID NO: 38          moltype = DNA  length = 65
FEATURE                Location/Qualifiers
source                 1..65
                       mol_type = unassigned DNA
                       organism = Nasonia vitripennis
SEQUENCE: 38
cttgtaatgc ggccgtgtaa ataatttaca cgtcggtctc aagcccgata acgcagaga    60
gcaag                                                                65

SEQ ID NO: 39          moltype = DNA  length = 76
FEATURE                Location/Qualifiers
misc_feature           1..76
                       note = Twister ribozyme from an environmental sample
source                 1..76
                       mol_type = unassigned DNA
                       organism = unidentified
SEQUENCE: 39
ggcaataaag cggttacaag cccgcaaaaa tagcagagta atgtcgcgat agcgcggcat    60
taatgcagct ttattg                                                    76

SEQ ID NO: 40          moltype = DNA  length = 65
FEATURE                Location/Qualifiers
```

```
misc_feature            1..65
                        note = Mutant twister ribozyme sequence from N. vitripennis
source                  1..65
                        mol_type = other DNA
                        organism = synthetic construct
SEQUENCE: 40
cttgtgatgc ggccgtgtaa ataatttaca cgtcggtctc aagcccgata aacgcagaga    60
gcaag                                                                65

SEQ ID NO: 41           moltype = DNA  length = 97
FEATURE                 Location/Qualifiers
misc_feature            1..97
                        note = N117 hammerhead ribozyme
source                  1..97
                        mol_type = other DNA
                        organism = synthetic construct
SEQUENCE: 41
ccgcggctga gatgcaggta catcccactg atgagtccca aataggacga aacgcgcttc    60
ggtgcgtctg ggattccact gctatccacg cggccgc                             97

SEQ ID NO: 42           moltype = DNA  length = 144
FEATURE                 Location/Qualifiers
misc_feature            1..144
                        note = Mutant N117 hammerhead ribozyme placed downstream of
                         start codon (frame 3)
source                  1..144
                        mol_type = other DNA
                        organism = synthetic construct
SEQUENCE: 42
gaattcgcca ccatggtgag caagggcgag gagctgttca ccccgcggct gagatgcagg    60
tacatcccac tgatgagtcc caaacaggac gaaacgcgct tcggtgcgtc tgggattcca   120
ctgctatcca cgcggccgct cggc                                          144

SEQ ID NO: 43           moltype = DNA  length = 147
FEATURE                 Location/Qualifiers
misc_feature            1..147
                        note = Mutant N117 hammerhead ribozyme placed downstream of
                         start codon (frame 2)
source                  1..147
                        mol_type = other DNA
                        organism = synthetic construct
SEQUENCE: 43
gaattcgcca ccatggtgag caagggcgag gagctgttca ccaccgcggc tgagatgcag    60
gtacatccca ctgatgagtc ccaaacagga cgaaacgcgc ttcggtgcgt ctgggattcc   120
actgctatcc acgcggccgc aatcggc                                       147

SEQ ID NO: 44           moltype = DNA  length = 147
FEATURE                 Location/Qualifiers
misc_feature            1..147
                        note = Mutant N117 hammerhead ribozyme placed downstream of
                         start codon (frame 1)
source                  1..147
                        mol_type = other DNA
                        organism = synthetic construct
SEQUENCE: 44
gaattcgcca ccatggtgag caagggcgag gagctgttca ccaaccgcgg ctgagatgca    60
ggtacatccc actgatgagt cccaaacagg acgaaacgcg cttcggtgcg tctgggattc   120
cactgctatc cacgcggccg catcggc                                       147

SEQ ID NO: 45           moltype = AA  length = 48
FEATURE                 Location/Qualifiers
REGION                  1..48
                        note = Translation of N117 hammerhead ribozyme
source                  1..48
                        mol_type = protein
                        organism = synthetic construct
SEQUENCE: 45
MQVHPTDESQ IGRNALRCVW DSTAIHAAAM APKKKRKVKI PGNSLAVV                 48

SEQ ID NO: 46           moltype = AA  length = 83
FEATURE                 Location/Qualifiers
REGION                  1..83
                        note = Translation of mutant N117 hammerhead ribozyme
                         placed downstream of start codon (frame 3)
source                  1..83
                        mol_type = protein
                        organism = synthetic construct
SEQUENCE: 46
MVSKGEELFT PRLRCRYIPL MSPKQDETRF GASGIPLLST RPLGGSSGSG EGRGSLLTCG    60
```

```
DVEENPGPTD SLAVVLQRRD WEN                                              83

SEQ ID NO: 47           moltype = AA   length = 84
FEATURE                 Location/Qualifiers
REGION                  1..84
                        note = Translation of mutant N117 hammerhead ribozyme
                         placed downstream of start codon (frame 2)
source                  1..84
                        mol_type = protein
                        organism = synthetic construct
SEQUENCE: 47
MVSKGEELFT TAAEMQVHPT DESQTGRNAL RCVWDSTAIH AAAIGGSSGS GEGRGSLLTC  60
GDVEENPGPT DSLAVVLQRR DWEN                                        84

SEQ ID NO: 48           moltype = AA   length = 13
FEATURE                 Location/Qualifiers
REGION                  1..13
                        note = Translation of mutant N117 hammerhead ribozyme
                         placed downstream of start codon (frame 1; part 1)
source                  1..13
                        mol_type = protein
                        organism = synthetic construct
SEQUENCE: 48
MVSKGEELFT NRG                                                     13

SEQ ID NO: 49           moltype = DNA   length = 114
FEATURE                 Location/Qualifiers
misc_feature            1..114
                        note = hairpin ribozyme
source                  1..114
                        mol_type = other DNA
                        organism = synthetic construct
SEQUENCE: 49
ccgcggcaag gtgagaggcc aaccagagaa acacaagcga aagcttggta cattacctgg  60
tacgatcgaa agatcgtggt gggaaaccac ctggcagtcc accttggcgg ccgc        114

SEQ ID NO: 50           moltype = DNA   length = 155
FEATURE                 Location/Qualifiers
misc_feature            1..155
                        note = Mutant hairpin ribozyme placed downstream of start
                         codon (frame 3)
source                  1..155
                        mol_type = other DNA
                        organism = synthetic construct
SEQUENCE: 50
gaattcgcca ccatggtgag caagggcgag gagctgttca ccccgcggaa ggagagaggc  60
caaccagaga acacaagcg aaagcttggt acattacctg gtacgatcga agatcgtgg  120
tgggaaacca cctggcagtc ctccttgcgg ccgct                            155

SEQ ID NO: 51           moltype = DNA   length = 158
FEATURE                 Location/Qualifiers
misc_feature            1..158
                        note = Mutant hairpin ribozyme placed downstream of start
                         codon (frame 2)
source                  1..158
                        mol_type = other DNA
                        organism = synthetic construct
SEQUENCE: 51
gaattcgcca ccatggtgag caagggcgag gagctgttca ccaccgcgga aggagagagg  60
ccaaccagag aaacacaagc gaaagcttgg tacattacct ggtacgatcg aaagatcgtg 120
gtgggaaacc acctggcagt cctccttgcg gccgcaat                         158

SEQ ID NO: 52           moltype = DNA   length = 158
FEATURE                 Location/Qualifiers
misc_feature            1..158
                        note = Mutant hairpin ribozyme placed downstream of start
                         codon (frame 1)
source                  1..158
                        mol_type = other DNA
                        organism = synthetic construct
SEQUENCE: 52
gaattcgcca ccatggtgag caagggcgag gagctgttca ccaaccgcgg aaggagagag  60
gccaaccaga gaaacacaag cgaaagcttg gtacattacc tggtacgatc gaaagatcgt 120
ggtgggaaac cacctggcag tcctccttgc ggccgcat                         158

SEQ ID NO: 53           moltype = AA   length = 89
FEATURE                 Location/Qualifiers
REGION                  1..89
                        note = Translation of mutant hairpin ribozyme placed
```

```
                              downstream of start codon (frame 3)
source                        1..89
                              mol_type = protein
                              organism = synthetic construct
SEQUENCE: 53
MVSKGEELFT PRKERGQPEK HKRKLGTLPG TIERSWWETT WQSSLRPLGG SSGSGEGRGS    60
LLTCGDVEEN PGPTDSLAVV LQRRDWENP                                     89

SEQ ID NO: 54                 moltype = AA  length = 90
FEATURE                       Location/Qualifiers
REGION                        1..90
                              note = Translation of mutant hairpin ribozyme placed
                                downstream of start codon (frame 2)
source                        1..90
                              mol_type = protein
                              organism = synthetic construct
SEQUENCE: 54
MVSKGEELFT TAEGERPTRE TQAKAWYITW YDRKIVVGNH LAVLLAAAIG GSSGSGEGRG    60
SLLTCGDVEE NPGPTDSLAV VLQRRDWENP                                    90

SEQ ID NO: 55                 moltype = AA  length = 90
FEATURE                       Location/Qualifiers
REGION                        1..90
                              note = Translation of mutant hairpin ribozyme placed
                                downstream of start codon (frame 1)
source                        1..90
                              mol_type = protein
                              organism = synthetic construct
SEQUENCE: 55
MVSKGEELFT NRGRREANQR NTSESLVHYL VRSKDRGGKP PGSPPCGRIG GSSGSGEGRG    60
SLLTCGDVEE NPGPTDSLAV VLQRRDWENP                                    90

SEQ ID NO: 56                 moltype = AA  length = 6
FEATURE                       Location/Qualifiers
REGION                        1..6
                              note = Translation of mutant N117 hammerhead ribozyme
                                placed downstream of start codon (frame 1; part 2)
source                        1..6
                              mol_type = protein
                              organism = synthetic construct
SEQUENCE: 56
DAGTSH                                                               6

SEQ ID NO: 57                 moltype = AA  length = 62
FEATURE                       Location/Qualifiers
REGION                        1..62
                              note = Translation of mutant N117 hammerhead ribozyme
                                placed downstream of start codon (frame 1; part 3)
source                        1..62
                              mol_type = protein
                              organism = synthetic construct
SEQUENCE: 57
VPNRTKRASV RLGFHCYPRG RIGGSSGSGE GRGSLLTCGD VEENPGPTDS LAVVLQRRDW    60
EN                                                                   62
```

We claim:

1. A polynucleotide construct for reducing the expression of a target gene in response to an aptamer ligand, the polynucleotide construct comprising (a) the target gene coding sequence flanked by a 5' and a 3' untranslated region (UTR); and (b) a riboswitch that comprises a twister ribozyme linked by a stem to an aptamer; wherein the aptamer comprises at least one stem; wherein the stem sequence linking the twister ribozyme to the aptamer comprises sequence that forms the aptamer stem and the P3 stem of the twister ribozyme; and wherein the target gene is linked to the P1 stem of the twister ribozyme; and wherein the riboswitch is located in (i) the 5' UTR, (ii) the 3' UTR, or (iii) the target gene coding sequence, 3' of the start codon.

2. The polynucleotide construct of claim 1, wherein the aptamer binds a small molecule ligand.

3. The polynucleotide construct of claim 1, wherein the twister ribozyme is from *Nasonia vitripennis*.

4. The polynucleotide construct of claim 1, wherein the twister ribozyme comprises SEQ ID NO.:38.

5. The polynucleotide construct of claim 1, wherein the twister ribozyme is from an environmental sample.

6. The polynucleotide construct of claim 1, wherein the twister ribozyme comprises SEQ ID NO.:39.

7. The polynucleotide construct of claim 1, wherein the P1 stem of the twister ribozyme is 4 to 7 base pairs.

8. The polynucleotide construct claim 1, wherein the stem sequence linking the twister ribozyme to the aptamer is 3 to 7 base pairs long.

9. A method of reducing the expression of a target gene in response to a small molecule aptamer ligand comprising
   (a) introducing the polynucleotide construct of claim 1 into a cell, and
   (b) exposing the cell to the small molecule ligand that specifically binds the aptamer in an amount effective to decrease expression of the target gene.

10. The method of claim 9, wherein the riboswitch is located in the 5' UTR of the target gene.

11. The method of claim 9, wherein the riboswitch is located in the 3' UTR of the target gene.

12. The method of claim 9, wherein the riboswitch is located in the target gene coding sequence, the 3' of the start codon.

13. The method of claim 12, wherein the polynucleotide construct comprises a 2A peptide sequence located 3' of the riboswitch, between the riboswitch sequence and the target gene coding sequence.

14. The method of claim 9, wherein two or more of the riboswitches are located in the target gene.

15. The method of claim 14, wherein the two or more riboswitches comprise different aptamers that specifically bind to different small molecule ligands.

16. The method of claim 14, wherein the two or more riboswitches comprise the same aptamer.

17. The method of claim 9, wherein the polynucleotide construct is incorporated in a vector.

18. The method of claim 17, wherein the vector is a viral vector.

19. The method of claim 18, wherein the viral vector is selected from the group consisting of adenoviral vector, adeno-associated virus vector, and lentiviral vector.

20. The method of claim 17, wherein the vector is a non-viral vector.

21. A vector comprising the polynucleotide construct of claim 1.

22. The vector of claim 21, wherein the vector is a viral vector.

23. The vector of claim 22, wherein the viral vector is selected from the group consisting of adenoviral vector, adeno-associated virus vector, and lentiviral vector.

24. The vector of claim 21, wherein the vector is a non-viral vector.

25. The polynucleotide construct of claim 1, wherein, when riboswitch is located in the target gene coding sequence, 3' of the start codon, a 2A peptide sequence is located 3' of the riboswitch, between the riboswitch and the target gene coding sequence.

* * * * *